US010359427B2

(12) United States Patent
Van Wie et al.

(10) Patent No.: US 10,359,427 B2
(45) Date of Patent: Jul. 23, 2019

(54) DUAL IONOPHORE ION SELECTIVE ELECTRODE FOR DETECTING NON-IONIC MOLECULES, MACROMOLECULES AND CELLS

(71) Applicant: Washington State University, Pullman, WA (US)

(72) Inventors: Bernard John Van Wie, Pullman, WA (US); Xuesong Li, Zhanjiang (CN)

(73) Assignee: WASHINGTON STATE UNIVERSITY, Pullman, WA (US)

( * ) Notice: Subject to any disclaimer, the term of this patent is extended or adjusted under 35 U.S.C. 154(b) by 384 days.

(21) Appl. No.: 15/400,528

(22) Filed: Jan. 6, 2017

(65) Prior Publication Data
US 2017/0212118 A1 Jul. 27, 2017

Related U.S. Application Data

(60) Provisional application No. 62/276,336, filed on Jan. 8, 2016.

(51) Int. Cl.
| | |
|---|---|
| *G01N 33/574* | (2006.01) |
| *G01N 27/327* | (2006.01) |
| *G01N 27/333* | (2006.01) |

(52) U.S. Cl.
CPC ...... *G01N 33/57434* (2013.01); *G01N 27/3276* (2013.01); *G01N 27/333* (2013.01); *G01N 33/57492* (2013.01)

(58) Field of Classification Search
CPC .......... G01N 27/333; G01N 27/57434; G01N 27/57492; G01N 27/3276; G01N 27/4166; G01N 27/4167; G01N 27/301; G01N 27/302; G01N 27/3335; G01N 27/416; G01N 27/414; G01N 27/415; G01N 27/417
See application file for complete search history.

(56) References Cited

FOREIGN PATENT DOCUMENTS

WO    WO 94/25862    * 11/1994    ......... G01N 27/333

* cited by examiner

*Primary Examiner* — Gurpreet Kaur
(74) *Attorney, Agent, or Firm* — W&C IP

(57) ABSTRACT

Biosensor and method of using the biosensors for the detection of prostate cancer are provided. The biosensors include a dual ionophore ion selective electrode for detecting very low levels of prostate cancer antigens at early stages of prostate cancer development.

13 Claims, 10 Drawing Sheets

DUAL IONOPHORE ION SELECTIVE ELECTRODE FOR DETECTING NON-IONIC MOLECULES, MACROMOLECULES AND CELLS

CROSS-REFERENCE TO RELATED APPLICATIONS

This application claims benefit of U.S. provisional patent application 62/276,336, filed Jan. 8, 2016, the complete contents of which is hereby incorporated by reference.

STATEMENT OF FEDERALLY SPONSORED RESEARCH AND DEVELOPMENT

This invention was made with government support under Grant No. 1023121 awarded by the National Science Foundation. The United States government has certain rights in the invention.

BACKGROUND OF THE INVENTION

Field of the Invention

The invention generally relates to a biosensor for the detection of nonionic molecules, macromolecules and cells and has a particular application in the detection of prostate cancer. In particular, the invention provides a dual ionophore ion-selective electrode for detecting very low levels of prostate cancer antigens.

Background

A biosensor is an analytical device which is capable of converting a biochemical signal into a quantifiable electrical signal. Biosensors typically include a biological or biologically devised sensing element in contact with a suitable transducer element. Recently, biosensors have begun to play an important role in medical research and clinical diagnosis, for example, in the detection of diabetes.

Prostate cancer is the most common cancer and one of the leading causes of cancer death among men in America. According to the Centers for Disease Control and Prevention (CDC), in 2012, 177,489 men in the United States were diagnosed with prostate cancer, and 27,244 men died from prostate cancer. Early diagnosis is crucial for patient survival.

The common methods of diagnosis for prostate cancer include prostate biopsies, transrectal ultrasounds and biomarker blood tests. However, prostate biopsies are invasive and uncomfortable, and transrectal ultrasounds sometimes have poor tissue resolution. Traditional cancer biomarker detection methods, including radioimmunoassays, enzyme-linked immunosorbent assays, electrochemical immunosorbent assays, fluorescence immunoassays, and chemiluminescence immunoassays, are widely used. However, these methods generally can only detect concentrations at or above the ng/mL level, which is insufficient for detecting very early stage cancer. Furthermore, performing methods such as ELISA and CLIA requires a secondary marker, increasing their complexity and the time needed to perform the test, and radioimmunoassays also pose a radiological hazard.

Ion-selective electrodes (ISEs; also known as specific ion electrodes, SIE), are transducers (sensors) that convert the activity of a specific ion dissolved in a solution into an electrical potential. Although they are very useful for measuring the concentration of ionic species across a membrane, extensions of their use to larger molecular species has met with limited success. While changes in signal upon the binding of a macromolecule to a ligand immobilized to a membrane can be detected, binding of the macromolecule also sterically blocks ionophore binding to the membrane, greatly decreasing the amount of signal as the measurement progresses.

There is a need to develop safer, less invasive and more accurate methods of detecting very low concentrations of prostate cancer biomarkers in order to permit the early diagnosis of prostate cancer. However, the use of conventional ISEs does not hold promise for solving this problem.

SUMMARY OF THE INVENTION

Features and advantages of the present invention will be set forth in the description that follows, and in part will be apparent from the description or may be learned by practice of the invention. The invention will be realized and attained by the compositions and methods particularly pointed out in the written description and claims hereof.

Described herein is a dual ionophore Ion-selective Electrode (di-ISE is), the design of which was inspired by living neuronal physiology in which signaling takes place as a result of the binding of a ligand to a receptor molecule, triggering membrane de-polarization and opening and closing of voltage gated K+ and Na+ channels. This approach was applied to the potentiometric responses in ISEs by utilizing two different ionophores. In the di-ISE, the two different ionophores are located in separated membrane compartments of the same electrode, with each membrane typically comprised of a porous polymer matrix with an organic liquid contained within the pores, and ionophores being soluble in the organic liquid such that the ionophores can transport ions from one side of the membrane to the other. Further, the top membranes of both compartments are both exposed to a single, common electrolytic solution, and the bottom membranes of both compartments are both exposed to a second different common electrolytic solution, so that the two compartments are electrically connected. The presence of the first and second ionophores in separate compartments, and the contact of both compartments with two different common electrolytic solutions from which ions migrate across the membranes, creates opposing concentration gradients across the membranes. At equilibration, the system establishes a resting voltage that corresponds to the relative permeability and transmembrane concentration gradients of each ion species. However, if a ligand or ligand conjugate is incorporated into a membrane covering one compartment of the di-ISE, the binding of an entity of interest to the ligand (e.g. by contact between the membrane bearing the ligand and a solution that contains the entity of interest) a complex is formed that blocks at least a portion of the membrane. This sterically hinders the flow of ions along the concentration gradient, leading to a voltage change. However, because the membrane always has a certain baseline ion-carrying capacity due to the presence of the second compartment, no matter how few ions are able to flow through the blocked membrane, a measurable voltage is still generated, and the change in voltage that occurs upon binding corresponds to the concentration of the entity of interest in the solution.

It is an object of this invention to provide a dual ionophore ion selective electrode (di-ISE) for detecting non-ionic molecules, macromolecules and cells, comprising I. a first chamber comprising (containing) a first membrane that is permeable to a first ion, wherein the first chamber contains an organic fluid comprising first ion ionophores, and II. a second chamber comprising (containing) a second membrane that is permeable to a second ion wherein the second chamber contains an organic fluid comprising second ion ionophores; wherein: the first membrane and the second membrane share a common exterior electrolytic fluid solution comprising the first ion; the first membrane and the second membrane share a common interior electrolytic fluid solution comprising the second ion; and the first membrane has an immobilized ligand specific for a binding site on a non-ionic molecule, macromolecule or cell, the immobilized ligand being located on a side facing the exterior electrolytic fluid solution. In some aspects, the immobilized ligand is specific for Prostate Circulating Tumor Cells (PCTCs). In other aspects, the first ion is K+ and the second ion is Na+. In further aspects, the first ion ionophores are valinomycin and the second ion ionophores are sodium ionophore X (NaX). In additional aspects, the binding site is prostate-specific membrane antigen (PSMA). In yet further aspects, the ligand is TG97. In other aspects, the TG97 is in the form of Cholesterol-PEG-TG97 (CPT).

The invention also provides methods of detecting PCTCs in a biological sample from a subject in need thereof, comprising A. providing a dual ionophore ion selective electrode (di-ISE) for detecting prostate cancer cells, comprising I. a first chamber comprising a first membrane that is permeable to a first ion, wherein the first chamber contains an organic fluid comprising first ion ionophores, and II. a second chamber comprising a second membrane that is permeable to a second ion, wherein the second chamber contains an organic fluid comprising second ion ionophores; and wherein: the first membrane and the second membrane share a common exterior electrolytic fluid solution comprising the first ion; the first membrane and the second membrane share a common interior electrolytic fluid solution comprising the second ion; and the first exterior membrane has an immobilized ligand for a binding site on PCTCs, the immobilized ligand being located on a side facing the exterior electrolytic fluid solution; B. measuring a baseline voltage generated by the di-ISE; C. contacting the first membrane with the biological sample on the exterior side for a period of time and under conditions which allow PCTCs present in the biological sample to bind to the immobilized ligand; and D. detecting a change in voltage upon said step of contacting, wherein a change in voltage is indicative of the binding of PCTCs to the exterior side of the first membrane and the presence of PCTCs in the biological sample. In some aspects, the first ion is K+ and the second ion is Na+. In other aspects, the first ionophores are valinomycin and the second ionophores are sodium ionophore X (NaX). In yet other aspects, the binding site is prostate-specific membrane antigen (PSMA). In additional aspects, the ligand is TG97. In yet further aspects, the TG97 is in the form of Cholesterol-PEG-TG97 (CPT).

DETAILED DESCRIPTION

The present disclosure provides biosensors for detecting very low levels of prostate cancer biomarkers. The biosensors solve the ion flow problem of ISEs (described above) by incorporating two ISEs using two different ionophores into a single device, a dual ionophore ion selective electrode (di-ISE). By "ionophore" we mean any chemical species that reversibly binds a particular type of ion and is able to transport the ion across a membrane.

Figure 1:
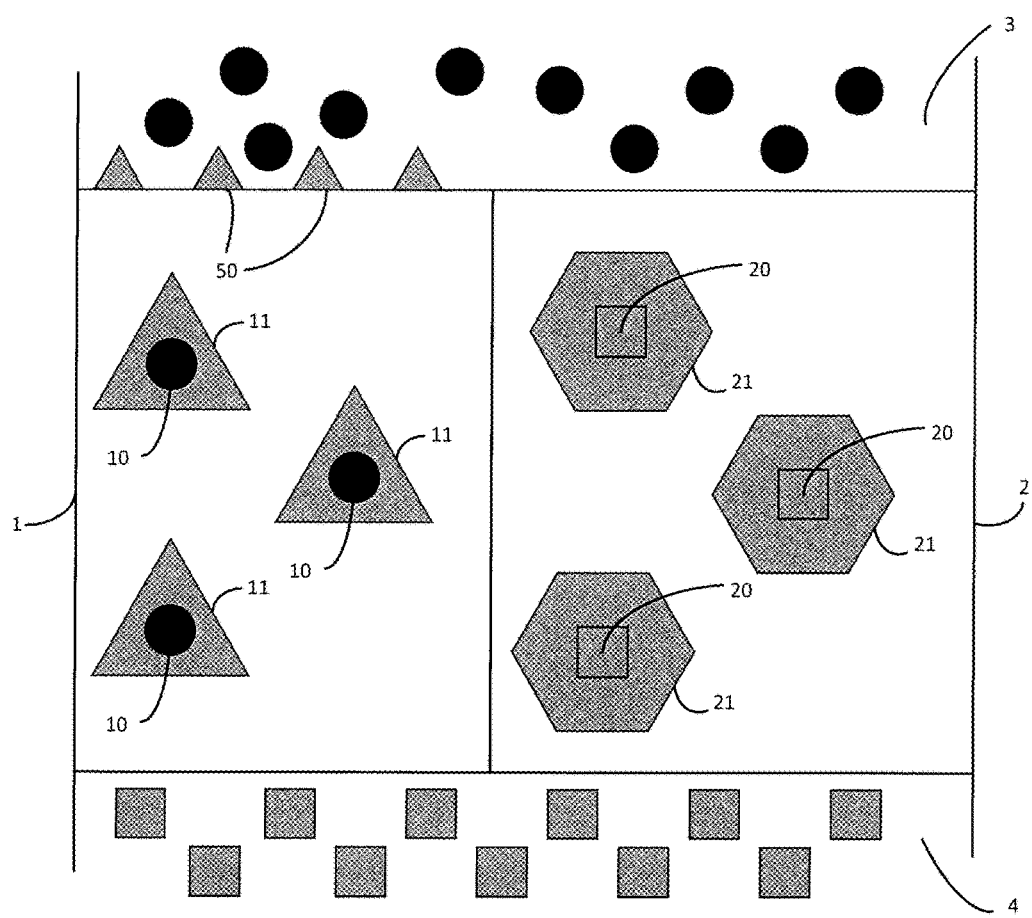
FIG. 1. Schematic representation of a di-ISE.

The di-ISE is illustrated schematically in FIG. 1, the electrode contains two compartments (chambers), compartment 1 and compartment 2, each of which contains, in a liquid solution, a different ionophore. Compartment 1 consists of a membrane in which first soluble ionophore 11 and compartment 2 contains second soluble ionophore 21. Ionophores 11 and 21 comprise or are associated with first ions 10 and second ions 20, respectively. Compartments 1 and 2 share two common solutions, "exterior" solution 3 (depicted as at the "top" of the device) and "interior" solution 4 (depicted as at the "bottom" of the device). Exterior solution 3 is an electrolytic solution containing a high concentration of first ion 10, e.g. from about 0.05 to about 0.15 M, i.e. about 0.05, 0.06, 0.07, 0.08, 0.09, 1.0, 1.2, 1.2, 1.3, 1.4 or 1.5 M. Interior solution 4 is an electrolytic solution containing a high concentration of second ion 20, e.g. from about 0.05 to about 0.15 M, i.e. about 0.05, 0.06, 0.07, 0.08, 0.09, 1.0, 1.2, 1.2, 1.3, 1.4 or 1. 5M.

The concentration of ionophore 11 within compartment 1 will vary according to the identity and characteristics of the ionophore, but generally ranges from about 0.1 to about 3% by weight (i.e. about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0% or more by weight). The concentration of ionophore 21 within compartment 2 will vary according to the identity and characteristics of the ionophore, but generally ranges from about 0.1 to about 3% by weight(i.e. about 0.1 or less, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9 or 3.0% or more by weight).

In an exemplary aspect, the two compartments contain ionophores selective for the ion pair K+ and Na+, for example, valinomycin (which is selective for K+) and sodium ionophore X (NaX, which is selective for Na+). However, other types of ions and ion selective ionophores or ion exchangers for those ions may be employed, and, if K+ and Na+ are selected, other K+ and Na+ selective ionophores may be used. Examples of ions which may be employed and corresponding ionophores are vast and include but are not limited to: Mg++ and magnesium ionophore IV (N,N',N"-Tris[3-(heptylmethylamino)-3-oxopropionyl]-8,8'-iminodioctylamine), Ca++ and calcium ionophore V (10,19-Bis[(octadecylcarbamoyl)-methoxyacetyl]-1,4,7,13,16-pentaoxa-10,19-diazacycloheneicosane), quaternary amines and dinonylnaphthalenesulfonic (DNNS) acid counter ions, NH4+ and Ammonium ionophore I (Nonactin), Cu(II) and Copper(II) ionophore I o-Xylylenebis(N,N-diisobutyldithiocar-bamate), Cl— and silver chloride, NO3- and nitrate ionophore VI (9-Hexadecyl-1,7,11,17-tetraoxa-2,6,12,16-tetraazacycloeicosane), and H+ and tridodecylamine.

The devices of the invention comprise at least one ligand that is specific for binding to an entity of interest (50 in FIG. 1). The ligand is immobilized on the side of an exterior membrane that is exposed to exterior solution 3 or one of the two compartments. In an exemplary aspect as illustrated herein, ligand 50 is immobilized on the outer surface of membrane 1. In some aspects, the entity of interest is Prostate Circulating Tumor Cells (PCTCs). Thus, at least one ligand binding site or molecule on the surface of PCTCs is specifically recognized by and binds to the at least one ligand molecule attached to the membrane. The at least one ligand binding site or molecule may be a hapten, an antigen or antigenic region, a protein or targeted segment thereof, a surface chemical group, an oligosaccharide, a lipid, an antibody, an aptamer, an oligomer or oligonucleotide, etc. or any other type of binding site for a ligand, or a combination of one or more of these. Binding may be substantially irreversible or reversible, but if reversible, the Kd of binding is at least in the range of from about $10^{-6}$ to about $10^{-10}$ molar (e.g. about $10^{-5}$, $10^{-6}$, $10^{-7}$, $10^{-8}$, $10^{-9}$, $10^{-10}$ or $10^{-11}$ M).

Suitable ligand binding sites/molecules on PCTCs include but are not limited to, for example: prostate-specific membrane antigen (PSMA), prostatic acid phosphatase (PAP), prostate stem cell antigen (PSCA), T cell receptor gamma alternate reading frame protein (TARP), transient receptor potential (trp)-p8, six-transmembrane epithelial antigen of the prostate 1 (STEAP1), etc.; androgen binding sites, in which case the ligand affixed to the membrane of the device may be an androgen or androgen derivative (e.g. modified to increase specificity and/or to make binding irreversible); various cancer or other disease markers; etc.

In one aspect, the ligand binding site/molecule is the cell-surface protein PSMA, in which case the ligand affixed to the membrane of the device is a molecule that binds to PSMA, and may be, for example: an inhibitor of PSMA such as TG97 (see FIG. 7); an antibody or aptamer specific for binding to and/or inhibiting PSMA. In addition to TG97, exemplary PSMA inhibitors are described in US patent applications 20140241985 and 20160030605 (whether or not they are chelated and/or labeled), in issued U.S. Pat. No. 9,422,234 (whether or not associated with a nanoparticle), any of the urea classes of inhibitors of PSMA, e.g. those described in issued U.S. Pat. No. 9,371,360; a peptidometic inhibitor such as those described in issued U.S. Pat. No. 9,328,129; etc., and others. The complete contents of each of the foregoing patents and patent applications are hereby incorporated by reference in entirety.

The PCTC ligand is present at an exterior or outside surface of a membrane of the device, e.g. at an exterior surface of the device that is capable of being exposed to a solution in a manner that permits molecules in the solution (usually an aqueous solution that is or contains a biological sample) to come into contact with the ligand. In some aspects, the PCTC ligand itself is directly attached to the membrane. In other aspects, the ligand is part of a ligand conjugate and is attached via one or more other molecules which function as anchors and/or linkers/spacers between the ligand and the membrane. In some aspects, a linker is a bifunctional spacer molecule which contains on one end an anchoring group for attachment to the membrane, or which is otherwise attachable to the membrane, and having another end or portion or chemical group that is attachable to the ligand. For example, the ligand may be attached or conjugated to one or more other molecules that are readily incorporated into the membrane, and/or readily attached to the membrane via a chemical bond, etc. Conjugate (conjugating) refers to coupling a first unit to a second unit and includes, e.g. covalently bonding one molecule to another molecule (for example, directly or via a linker molecule), noncovalently bonding one molecule to another (e.g. electrostatically bonding) (see, for example, U.S. Pat. No. 6,921,496, which discloses methods for electrostatic conjugation), non-covalently bonding one molecule to another molecule by hydrogen bonding, non-covalently bonding one molecule to another molecule by van der Waals forces, and any and all combinations of such couplings.

Such molecules may also act as spacers or linkers to hold the ligand away from the surface of the membrane to facilitate exposure of the ligand to PCTCs, i.e. to act as a tether. Further, two or more molecules may be used in tandem in such a tether, e.g. one (a first) of which attaches directly to the membrane and another (a second) of which binds to the first molecule and to the PCTC ligand, linking them together. The second molecule may function to facilitate chemical attachment of the PCTC ligand to the first membrane binding molecule, and/or to add to the length of the tether to increase the distance of the PCTC ligand from the membrane surface, or both. The ligand may also be attached to the membrane via nanoparticles or microsphere beads.

Exemplary molecules that may be utilized in a conjugate to bind directly to a membrane of the device of the invention include any molecules typically used to stabilize or anchor into membranes. These may include but are not limited to: cholesterol and various cholesterol derivatives (e.g. lipophilic soluble derivatives); lipids; peptide and polypeptide chains; lipophilic polymers, and various other molecules typically used to stabilize or anchor molecules of interest into a membrane. Polymers e.g. polyethers such as polyethylene glycol (PEG) polymers may be used to reduce non-specific absorption to the membrane. It is also possible to chemically attach to the membrane and still be hydrophilic by making two polymers and mixing e.g., graft the polyethylene glycol to polyvinyl chloride and upon mixing the grafted material will be in the water layer. Or one can modify the polyvinyl chloride membrane with polyvinyl acetate or acrylic acid groups and couple to these on the surface. Or one can plasma treat the membrane to make functional groups to which other molecules can be coupled.

Examples of molecules and/or chemical linkages that may be used to cross-link the molecule that binds to the membrane and the PCTC ligand in order to chemically join them include but are not limited to: various amine-reactive chemical groups, N-hydroxysuccinimide esters (NHS esters), NHS-reactive chemical groups, imidoesters, carboxylic acid-reactive chemical groups, carbodiimides such as (1-ethyl-3-[3-dimethylaminopropyl]carbodiimide hydrochloride (EDC or EDAC) and N,N'-dicyclohexylcarbodiimide (DCC), sulfhydryl-reactive chemical groups, maleimides, haloacetyls, pyridyl disulfides, carbonyl-reactive chemical groups, aldehydes), hydrazides, alkoxyamines, photoreactive groups Michael acceptors, and other molecules or chemical linkages that are typically used in scavenger resin technology, etc.

Further linking strategies are described, for example, in published US patent applications 20160333053; 20160331822; 20160324975 and 20160291014; and issued U.S. Pat. Nos. 9,513,295; 9,493,538; 9,433,638 and 6,362,254, the complete contents of each of which are hereby incorporated by reference in entirety.

The ligand or ligand conjugate is generally substantially immobilized (affixed, attached, anchored, etc.) on the exterior membrane surface at the interface of the exterior membrane and the common exterior ion-containing solution to which it is exposed. Immobilization may occur by any suitable means, for example, by covalent, ionic or hydrophobic bonds, or hydrogen bonding or chemical adhesive attachment; by being built into the membrane during membrane construction and thus forming part of the membrane itself, or by any number of cross-linker molecules or antibody or bispecific antibody attachment. While the ligand is substantially immobilized on or at the membrane surface, this does not preclude lateral migration of along a surface of the membrane or tumbling of the molecule within the membrane.

The invention also encompasses methods of detecting PCTCs in biological or other relevant samples. The method involves providing a di-ISE as described herein, the di-ISE having at least one membrane that is accessible to or contactable by a biological sample of interest (e.g. a sample that is known or suspected of containing PCTCs). The membrane comprises at least one ligand of a binding site on PCTCs. The di-ISE membrane and the sample are placed in contact with each other. For example, the di-ISE or suitable (relevant) portions thereof, is/are immersed or submerged in the sample so that the sample contacts the membrane. Contact is made under conditions that allow binding to occur between the ligand on the membrane and the binding site on a PCTC, so that the PCTC is sequestered on the membrane. The amount of time required for contact between the sample and membrane generally ranges from a few seconds to about 30 min (e.g. about 1, 5, 10, 15, 20, 25 or 30 minutes), and can vary depending on the volume of solution containing the PCTC, the proximity of the PCTC, or other cell or molecule to be detected through similar binding, and whether migration occurs purely by sedimentation, diffusion, or convective mixing whether through stirring or turbulent flow related mixing, but generally the goal is for the binding and associated sensing to occur in range of seconds to a few minutes (for example, about 1 to 59 seconds, or about 1, 2, 3, 4, 5, 6, 7, 8, 9, 10 minutes . As described above, sequestration of PCTCs on the membrane sterically occludes the membrane so that fewer ions can pass through, resulting in a detectable, measurable change in voltage that is correlated with the concentration of PCTCs in the sample.

Suitable biological samples are generally liquid in nature, or are diluted, dissolved or suspended in a physiologically/biologically compatible buffer prior to practicing the method. Exemplary biological samples include but are not limited to: urine, blood, saliva, plasma, synovial, spinal, pericardial, lymphoid or other bodily fluid, etc. Exemplary physiologically/biologically compatible buffers include but are not limited to those that buffer at or near a pH of 7.4 (e.g. from about 7.0 to about 7.8) and include: phosphate buffer, carbonate buffers, Goode's buffers that buffer in this region (e.g. MOPSO, cholamine chloride, MOPS, BES, TES, HEPES, DIPSO, MOBS, TAPSO, TEA and POPSO); and others.

Types or categories of prostate cancer that can be detected using the methods and devices disclosed herein include but are not limited to: acinar adenocarcinomas; ductal adenocarcinomas; transitional cell (or urothelial) cancers; squamous cell cancers; small cell prostate cancers; low-grade, low-stage cancers ("indolent" cancers); various primary and metastatic tumor cells, etc.

Using the methods described herein, concentrations or levels of PCTCs ranging from 1 to about 1000 can be detected depending on the size and number of independent di-ISE membranes used for detection, i.e. levels as low as 1 PCTC can be detected in biological samples if a di-ISE similar in diameter to the PCTC is used. Thus, from 1 to about 1000 PCTCs can be detected, e.g. from 1, or about 100, 200, 300, 400, 500, 600, 700, 800, 900 or 1000 or more.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting. Any other cell type, protein or molecular species, especially higher molecular weight species, with identifiable binding sites can be detected as well with a similar ligand arrangement with linkage to the membrane and a receptor for the cell binding site.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise. These are typical ranges only and values outside, above and below, these ranges may be possible.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.)...".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Example 1

Neuron-Like Dual Ionophore Ion-Selective Electrode for Detecting Proteins

In this Example, a new dual ionophore Ion-selective Electrode or di-ISE is described which mimics the nerve cell or neuronal membrane that responds with electronic signals when proteins bind to a membrane in order to detect the target protein. To mimic nerve cell sensing, robust membranes which are stable for weeks or months are made by replacing neuron lipid bilayer membranes with organic liquid membranes suspended in a polymer matrix. K+ ionophores and Na+ ionophores are used to avoid the need for isolating large molecular weight neuronal ion channels. The ionophores are confined to separate membranes, but the separate membranes are electrically connected by being in contact with the same inside and outside solutions. K+ and Na+ gradients are in opposing directions as is the case for living neurons.

In this exemplary aspect, into the K+ side of the membrane is inserted cholesterol-Polyethylene glycol-Biotin (CPB) as a ligand that is a representative bio-detection molecule. When the targeted protein (streptavidin in this case) binds to CPB on the K+ side of the membrane, potassium flux will decrease changing the transmembrane voltage from a resting potential to a positive or negative value depending on which side contains K+ and which contains Na+. Di-ISEs created in this fashion can theoretically shift in measurable potential changing by as much as 150 mV depending on the amount of analyte bound and relative concentrations of ions within the inside and outside solutions. A theoretical basis is provided based on a modification of the Goldman-Hodgkin-Katz relationship for living neurons.

Protein Sensor—Dual Ionophore ISE Theory

Figure 2A:
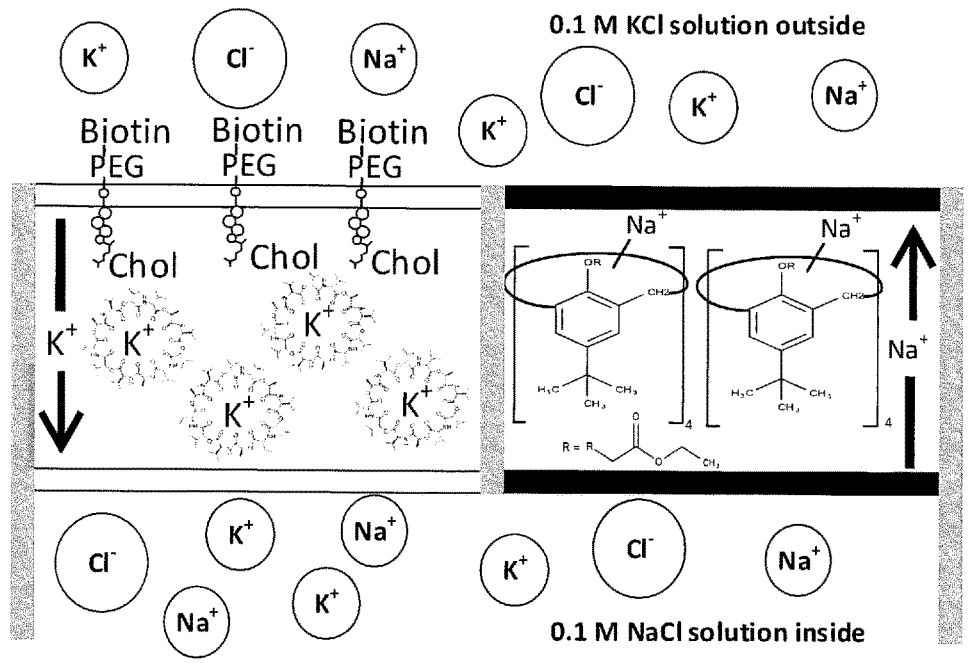
FIGS. 2A and B. Protein biosensor di-ISE sensing concept: (A) A dual ionophore ion-selective electrode (di-ISE) is designed to contain two separate membrane chambers with a common interior electrolytic fluid solution and a common outside electrolytic fluid solution; (B) Capturing Streptavidin-AlexaFluor®488 conjugate through Biotin-Streptavidin ligand-receptor mechanics prevents K+ ion from being transferred, resulting in a measurable membrane potential shift.

The dual ionophore ion selective electrode (di-ISE) concept is inspired by ion channel controlled transmembrane voltage regulation in living neuronal physiology. FIG. 2A shows a schematic diagram of an exemplary di-ISE protein biosensor similar to the general design shown in FIG. 1. The di-ISE includes two separated membrane chambers. One chamber contains a K+ ionophore (in this case valinomycin) and the other chamber contains a Na+ ionophore (in this case Sodium ionophore X, NaX). The two separated chambers are exposed to the same inside solution, in this case 0.1 M NaCl, and outside solution, in this case 0.1 M KCl. As illustrated in FIG. 2A, the ligand Cholesterol-PEG-Biotin (CPB) was inserted into the K+ ionophore side of the membrane by the insertion procedure developed by Shishkanova et al. (Shishkanova, et al. Biosens Bioelectron, 2007. 22(11): p. 2712-7). The Na+ gradient and the K+ gradient are in the opposite direction (indicated by arrows), so changes in the relative permeability and ion concentrations modulates membrane potential. Therefore, the amount of ligand CPB complexes and the starting ratio of ionophores dominate the changing of voltages, like in a living neuron.

Figure 2B:
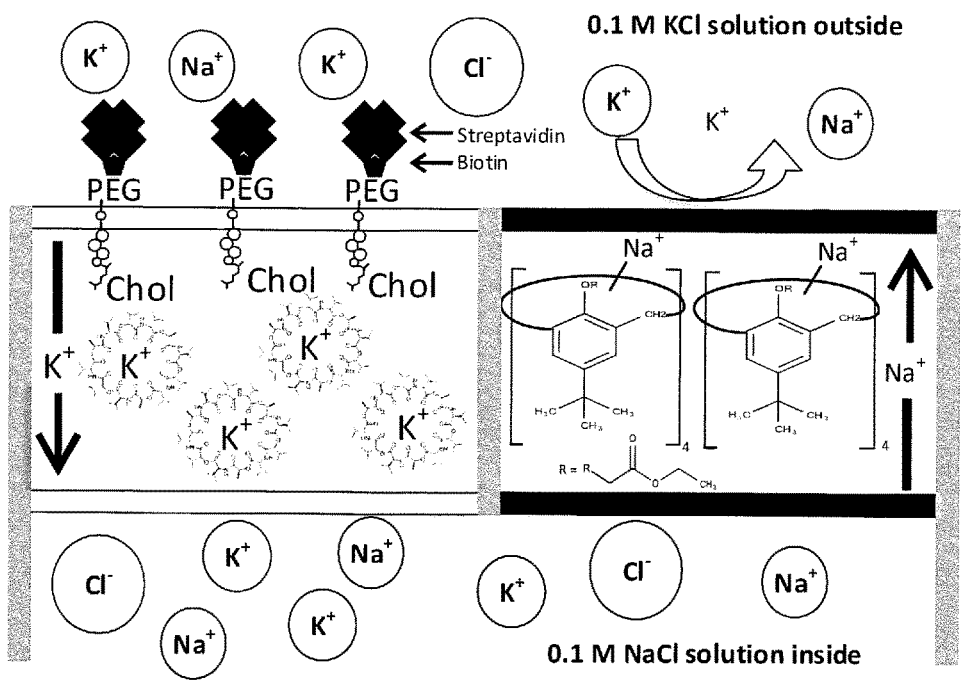

FIG. 2B shows how the sensor reacts when exposed to a sample containing an analyte, in this case streptavidin-AlexaFluor®488 for detection. In the presence of the free analyte, streptavidin-AlexaFluor®488 binds to biotin on the left side of the membrane. The biotin-streptavidin conjugate partially blocks the membrane as its surface concentration increases. This allows far fewer K+ ions to flow through the membrane than Na+ ions and causes a voltage change toward the Na+ equilibrium potential. The resulting voltage depends on the K+ and Na+ transmembrane concentration gradients and how much K+ ionophore is prevented from participating in K+ transport across the membrane because of bound streptavidin. Because the membrane always has a certain baseline ion-carrying capacity, i.e., due to the Na+ ionophore, no matter how little K+ ionophore is available for transporting ions, there will still be a measurable voltage.

Methods

Reagents

The membrane reagent cocktails were composed of high molecular weight Poly (vinyl chloride) (PVC) of Selectophore grade (Fluka), Dioctyl phthalate (DOP) (Aldrich), tetrahydrofuran (THF) (Fluka), Benzene (Fisher Scientific Company), Cholesterol polyethylene glycol biotin (CPB) (molecular weight 5000, NANOCS), Valinomycin, a K+ ionophore (A.G. Scientific. Inc.), and Sodium Ionophore X (NaX) (Fluka). One of protein samples was 100% bovine gelatin (Bernard Jensen Products). Another was Streptavidin and Streptavidin-FITC from *Streptomyces avidinii* (Sigma Aldrich), and Streptavidin AlexaFluor®488 conjugate (Thermo Fisher Scientific). Materials for constructing original designed Ion-selective electrode cartridges included beverage clear Tygon® PVC tubing of 0.25" inner diameter and 0.375" outer diameter (Fisher brand), durable nylon tight-seal barbed tube fitting Wye connector for 0.25" diameter tubing (McMaster-Carr), ethylene propylene diene monomer (EPDM) tapered plug with a 0.188" small end and a 0.344" large end (Rubber Dynamics), 18G silver wire of 99.99% purity (Artbeads, Wash.), and FeCl3/HCl PC-Board Etching solution to make Ag/AgCl electrodes (GC Thorson, Inc., Rockford, Ill.).

Immobilization of CPB into PVC Membrane- Extraction Protocol

The membrane was washed with DI water. The membrane cocktail was made with 1.65 mg PVC, 3.3 mg DOP, 100 µL of benzene and 300 µL of THF. CPB powder was dissolved in water. Then 500 µL of aqueous solution of CPB was added at final concentrations of 0.1 nM, 1 nM, 10 nM, and 100 nM with membrane cocktail in 1.5 mL Eppendorf tubes. The combined solution in Eppendorf tubes was vigorously shaken for 2 min and centrifuged at 12K rpm for 10 min. They were then put in a sonicator for 30 min. The tubes were opened in a closed ice bucket to slow evaporate the membrane solvent for about one week. Then the bottom of the Eppendorf tube was cut off exposing a thin membrane formed on the top of the aqueous layer. Inverting the Eppendorf tube, the membrane was ready to use by washing with DI water.

Electrode Construction

Figure 3A:
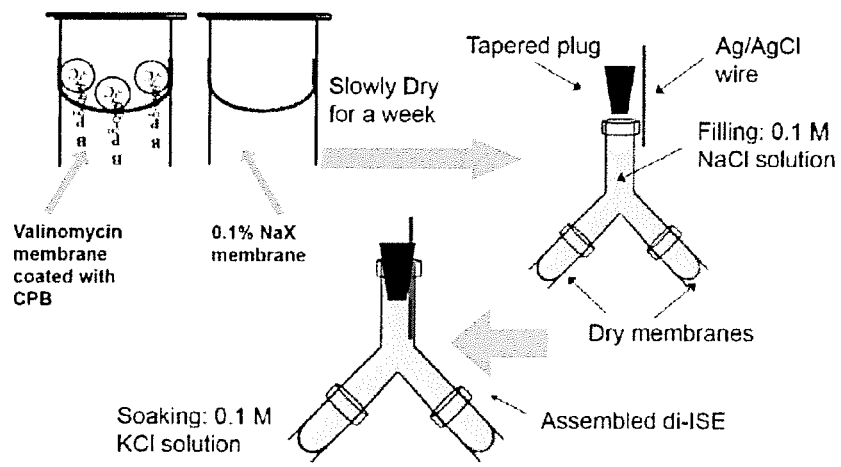
FIGS. 3A and B. Electrodes construction. (A) Electrodes were constructed with two types of ionophore membranes, Y-connector, tapered plugs, and Ag/AgCl wires. (B) The schematic diagram shows the measurement setup with di-ISEs, reference electrode and potentiometer connected to a computer.
Figure 3B:
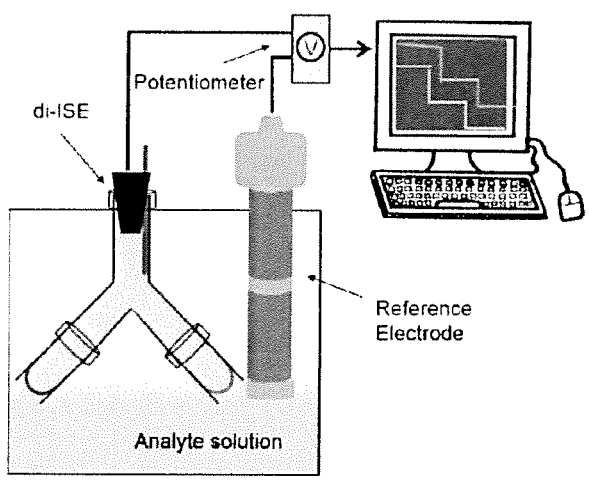

For the construction of the protein sensor di-ISE, the electrode membranes included the valinomycin ionophore at 1 wt % for the K+ side of the membrane and 0.1 wt % NaX for the Na+ side. FIGS. 3A and B is a schematic diagram illustrating electrode construction. One point of innovation in this new di-ISE is the use of two types of ionophore membranes that are connected electrically by liquid by a Y-shaped connector sharing the same filling solution of 0.1 M NaCl; but the two membrane halves are separated from each other so that when analyte binds to the K+ side it only interferes with the K+ permeability and not the Na+ permeability—the transmembrane potential still is the collective potential established by these two sections of membrane. Silver wires of 0.04" diameter were etched with ferric chloride for 20 minutes to form Ag/AgCl wires. Tapered plugs were used as caps to seal the Ag/AgCl wires inside the electrode bodies. The di-ISEs were soaked in 0.1 M KCl solution overnight before testing.

Apparatus

The inexpensive potentiometer was designed with miniature (7 cm×4 cm×1 cm), and an eight-channel high input impedance 12 bit A/D converter (resolution was 0.62 mV) for measuring the potential. The device was connected to a computer via a USB, and could hold up to eight ISE electrodes and the reference electrode using pin receptacles. Data were collected from digital reading and analyzed by converting voltage in Excel and normalizing data to a zero reading at 10-7 M K+.

Confocal Laser Scanning Microscopy

The LSM 510 META Laser Scanning Microscope (Carl Zeiss MicroImaging GmbH, Jena, Germany) was used to visualize Streptavidin-FITC under 10×, 25×, and 63× water immersion objectives. An argon laser was used to excite at 488 nm for Fluorescein isothiocyanate (FITC) or AlexaFluor®488, and an LP505 nm filter was used to collect the emission spectra. The special confocal scanning parameters were set up to make sure there was no fluorescent signal from background light for the untreated control membrane. The resolution was 1024×1024 pixels for the taking of all images. The pictures were edited by ZEN lite 2012 software.

Protein Biosensor Testing

Di-ISE Characterization

The electrode calibration curve was measured using the NRL potentiometer device at room temperature. For the protein biosensor, both 1 wt % valinomycin//0.1 wt % NaX di-ISEs and 1 wt % valinomycin+10 nM CPB II 0.1 wt % NaX di-ISEs were tested where the symbol "//" separates the two sections of electrically connected membranes. Both membrane sides of the electrode were dipped into a continuously stirred crucible with 50 mL deionized nano-pure (DI) water. For all tests, the reference electrode was filled with 3 M NaCl. The response time was calculated as a rate of emf variation ($\Delta E/\Delta t$) by definition according to IUPAC [Macca, C., Analytica Chimica Acta, 2004. 512(2): p. 183-190; Buck, R. P. and E. Lindner, Pure & Applied Chemistry, 1994(66): p. 2527-2536]. The standard addition method (SAM) was used for linearity and limit of detection (LOD) studies for K+ concentrations from 10-7 M up to 10-1 M.

Di-ISE Behavior Modeling

Equation (1) was used for di-ISE behavior modeling $$E = E° + S \cdot \log\left[\frac{(C_{k,eff} \cdot a_k)_{outside}}{\lambda \cdot (C_{Na,eff} \cdot a_k)_{inside}}\right] + U \tag{1}$$

where: E is the membrane voltage, E° is the standard cell potential; the slope term, S, is RT/zF, i.e. at a temperature of 298 K and an ion charge of +1 the theoretical value is 59 mV/log[conc.]; $C_{i,eff}$ is the effective ionophore concentration for ion i, aK and aNa the activities of K+ and Na+ ions, U the undetermined coefficient used to model the limit of detection. The coefficient $\lambda$ is the ratio of valinomycin diffusion coefficient in dioctyl phthalate (DOP) compared to that of the sodium 10 (NaX) in DOP, and while unknown is estimated by non-linear modeling of the system parameters to obtain a best fit of the equation to experimental voltages vs. external solution ion activity data for a calibration curve for the di-ISE before use as a cell sensor. It is assumed that activities are approximately equal to concentrations in all cases. The coefficient $\alpha$ is the fraction of the external interfacial surface exposed to cells or cell simulants available for ion carriers transported through the bioaffinity membrane compartment holding valinomycin ionophores. $\alpha$ is determined by refitting the model, while holding $\lambda$ and U constant, after coverage of the surface by aluminum foil, microspheres or cells and represents the portion of the bioaffinity chamber covered or at least made inaccessible to the valinomycin ionophore.

For modeling CPB behaviors, Equation (2) was used:

$$C_{i,\mathit{eff}} = \alpha \cdot C_i \times \left(1 - \frac{K_{i,j} \cdot a_j}{K_{i,j} \cdot a_j + a_i}\right) + C_j \times \frac{K_{j,i} \cdot a_i}{K_{j,i} \cdot a_i + a_j} \quad (2)$$

The coefficient a is the fraction of the external interfacial surface exposed to protein or protein simulants available for to ion carriers transported through the bioaffinity membrane compartment holding valinomycin ionophores. The variables $a_i$ and $a_j$ are the activities of primary and interfering ions, and $K_{i,j}$ the selectivity coefficient for the ionophore for species I to interfering ion j.

Di-ISE Surface Coating Simulation

For simulating the behavior of di-ISE capture and sensing of proteins, the method used was to coat the K+ ionophore side of di-ISEs membrane with gelatin. Gelatin concentration was from 3.33-333 µM. After the K+ ionophore side of di-ISEs membrane was formed, it was soaked in the gelatin solution for 4 hours. After the K+ ionophore side of di-ISEs membrane was dry, 7 µL of Na+ ionophore PVC cocktail was applied on the other side to form the Na+ ionophore side of di-ISEs membrane. The concentration of di-ISE with the K+ ionophore was 1% valinomycin and the Na+ ionophore was 0.1% NaX. Eight di-ISEs served as controls, i.e., they were never coated with gelatin. The remaining electrodes were soaked in different concentration gelatin solution and tested by use of the SAM. Potentiometric data was collected.

Di-ISE Capture of Streptavidin Fluorescent Conjugates

To determine whether a sensor is a biosensor depends on two components: a bioreceptor and a transducer. The bioreceptor is capable of recognizing a specific target molecule; in our case cholesterol-polyethylene glycol-biotin (CPB) is the bioreceptor. The transducer converts the recognition event into a measurable signal; in our case di-ISE is the transducer. The first experiment was to make membranes containing different concentrations of CPB to test capture of fluorescent streptavidin. This exemplary di-ISE contains 1 w % valinomycin+10 nM CPB on the K+ side of the membrane and 0.1 w % NaX on the other side. The membranes were made of CPB concentrations from 1 nM to 300 nM. 150 µL of 300 nM fluorescent streptavidin was added onto the membrane surface and incubated at 37° C. for 30 min. Then membranes were washed with pH 7.4 PBS buffer three times. The fluorescent components were streptavidin AlexaFluor®488 and streptavidin FITC. The membrane-streptavidin conjugates were scanned by confocal laser scanning microscopy.

The second experiment tested the ability of di-ISE to capture protein. The K+ ionophore side of membrane surface was coated with various concentrations of CPB by both adsorption and extraction protocols. The di-ISEs consisted of K+ ionophore with CPB on one side of the membrane, and Na+ ionophore on the other side. After di-ISE calibration by adding KCl solution to reach a final concentration of 0.1 M, the streptavidin was added on the K+ ionophore side of membrane surface and incubated at 37° C. for 30 min. The concentration of streptavidin was 300 nM-3 µM. After incubation, the membranes were put back into the di-ISEs to test the ability of the K+ ionophore side of the membrane to pass K+ ions. The result was shown by monitoring of potential [mV] vs. time [s] on the SAM.

Results and Discussion

Di-ISE Surface Coating Simulation

Figure 4:
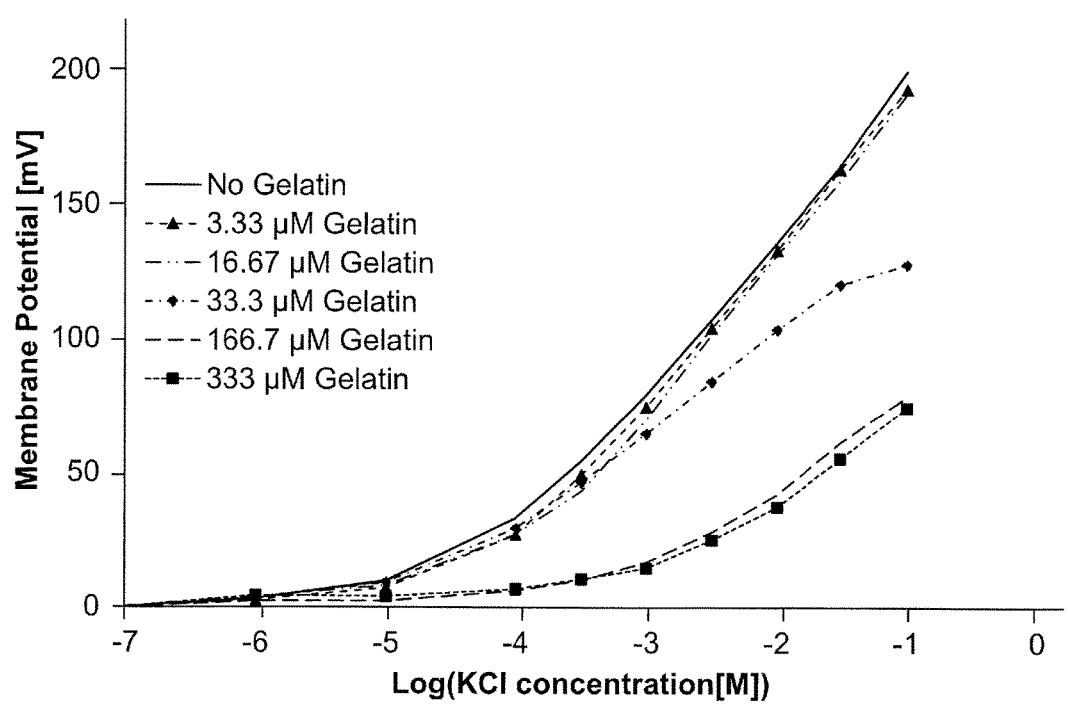
FIG. 4. Coating the K+ ionophore side with different concentrations of gelatin, the signal decreased with increasing gelatin concentrations simulating the binding of protein. The di-ISEs were comprised of 1 w % valinomycin in one membrane segment and 0.1 w % sodium ionophore X (NaX) in the other.

This experiment qualitatively simulates that when the di-ISE K+ ionophore membrane side is covered by protein, the membrane potential will be reduced in relation to the amount of coverage. In this experiment, gelatin was used as a protein simulate for coating the K+ ionophore side of the membrane surface without the need for a ligand. The results in FIG. 4 show when the surface is coated by lower concentrations of gelatin in the 3.33-16.67 µM range, the calibration curves are close to the controls which had no gelatin. The reason is that when the gelatin concentration is too low, the solution forms a thin porous covering of membrane surface, and therefore did not severely limit K+ ions from being transported to the surface. However, when the gelatin concentration is increased to 33.3 µM, the membrane potential shifts downward. Because part of the membrane is covered by gelatin, the ability to transfer K+ ions to the surface for subsequent transport through the membrane is reduced. When the membrane is coated with gelatin concentrations of 166.7 µM, the potential decreases even more. Finally, when the membrane is coated with 333 µM gelatin, the membrane potential stays nearly the same as indicating that after 166.7 µM, the membrane surface is saturated, and adding more gelatin will not reduce the voltage further either because of a base carrying capacity for K+ by the NaX side of the membrane, permeation of some K+ ions through gelatin matrix, of a combination. This result shows that binding of a protein, whether non-specifically or specifically with a ligand, to one side of the di-ISE affects the transport/permeability of mainly for the ionophore in the corresponding side of the di-ISE membrane.

Characterization

The basic properties of the new protein di-ISEs, for the base membrane and for that containing CPB were evaluated experimentally and by nonlinear curve fitting of calibration curves to an Equation (1) di-ISE model. The results showed that both electrodes respond to step changes in K+ concentration with the speed and sensitivity characteristic of typical ISEs with response times of 1.8 mV/sec and 0.7 mV/sec respectively, for the non-CPB and the CPB containing di-ISEs. The slopes of di-ISE calibration curves without and with CPB were 54.3 (N=10), and 41.1 (N=9), respectively for typical sets of di-ISE electrodes. For performing a non-linear curve fit using Equation (1), a literature value of the selectivity coefficient for the K+ ionophore for the Na+ ion, $K_{K,Na}$=0.0001 was used along with a value determined by the separate solution method for $K_{Na,K}$ of 0.035 [Haarsma, S. J., *New Dual Ionophore Immunosensor Concept: Modeling and Experimental Support*, in Gene & Linda Voiland School of Chemical Engineering and Bioengineering 2010, Washington State University: Pullman. p. 73]. Through a non-linear curve fit of equation (1) a diffusivity ratio, λ, of 0.85 and an undetermined coefficient U of 0.0127 were determined. Average agreement between the data and the model of 98%. The diffusivity ratio is in agreement with theory if it is considered that diffusivities of the large molecular weight ionophore molecules vary, according to the Stokes-Einstein equation, inversely with the square root of the molecular radii which are related to MWs, that of valinomycin being 1,111 and that of sodium ionophore X being 993. An estimated effective diameter of valinomycin is 1.6 nm, and the effective diameter of sodium ionophore X is 1.5 nm, so the ratio of valinomycin diffusion coefficient in DOP compared to that of the NaX in DOP, which gives a λ value equal to 1.07. Since molecular weights are close, the molecular radii are also close with that of the valinomycin being slightly higher and hence having a λ value just on the order of about 1.0 (0.85) is not surprising.

When considering the drop in voltage because of CPB presence on the surface, the steric hindrance to K+ ions reaching the interface, and thereby reducing the effective K+ ion permeability on the K+ ionophore side of the di-ISE, must be considered. First, from non-linear fitting of Equation (1) using the same U and values found for the di-ISE without CPB, a multiplier for the K+ ionophore concentration of 0.67 is determined to provide an excellent fit to the data with an average agreement with the highest four concentrations to within 97% without CPB and to within 99% with CPB; average absolute agreement including all data points is to within 3.1 mV without CPB and to within 0.46 mV with CPB (not shown). Decreasing the valinomycin present on the K+ carrying side of the membrane decreases the membrane potential. Effectively then, hindering participation of some fraction of the valinomycin molecules from participating in the K+ transport will have the same effect and that can happen by blocking part of the surface. This effect can be approximated by calculating the space occupied by the cholesterol inserted into the membrane as well as the PEG linker theoretically occupying the surface or perhaps sweeping the membrane-water interface. Cholesterol has a molecular length of 1.6 nm, and biotin size of 1.55 nm diameter. The PEG has a molecular width of 0.086 nm, and with a monomer length of 0.35 nm and a MW of 5000 g/mol for PEG-Biotin having a spacer arm 36.2 nm. Under ideal conditions, if cholesterol is inserted into the membrane, and the PEG-biotin occupies a fraction of the surface equal to its size, and each membrane contains 0.5 mL of 10 nM CPB there will be $3.0 \times 10^{12}$ CPB molecules on the membrane surface occupying a space of 9.4 mm$^2$ which is 18% of the membrane surface (51.5 mm$^2$). This is in reasonable agreement with the 0.67 value, which translates to 33% of the surface being covered, found by non-linear fitting of Eq. (1) especially since it is difficult to determine the real length of the PEG molecule because it can coil, fold, twist etc. and while sweeping the surface K+ ions are likely to be further hindered from passing through to the membrane where they will encounter an ionophore and be transported.

The curves also revealed the best K+ concentration ranges for use of the di-ISE. A K+ concentration must be selected that is compatible for analyte contained in test solutions and which provides a maximum difference in readings when analyte is added. Calibration curves show that the linear range of the measured calibration curve of di-ISEs were both between $10^{-3}$ and $10^{-1}$ M. The observed limit of detection (LOD) for both di-ISEs is $1.07 \times 10^{-4}$ M and $2.64 \times 10^{-4}$ M for the non CPB and CPB coated membranes, respectively, based on IUPAC recommendations outlined by Buck and Lindner [previously cited herein] as the concentration of K+ at the point of intersection of the extrapolated limit of the midrange and final low concentration level segments of the calibration plot. Hence, the di-ISEs should be used with external solutions containing K+ ion well above the LODs of $10^{-4}$. At the same time solutions containing as high a concentration of K+ as can be tolerated, because the calibration curves diverge as concentration increases. In biological solutions having K+ or Na+ concentrations in the 0.1 M range is not unusual, and therefore, the higher concentration may be selected. Too high of an ion concentration can cause problems with analyte and ion solubility, cell viability, if cells are present, incorrect folding of a protein being sensed, and reaching a point where activities are no longer approximately equal to concentration. These factors help guide use of di-ISEs.

Di-ISE Binding Streptavidin Fluorescent Conjugates

The next experiment showed that a membrane containing CPB as a bio-receptor has the ability to capture streptavidin. When 150 μL of 300 nM streptavidin AlexaFluor®488 was added to membranes coated with different membrane concentrations of CPB of 0, 1, 10 and 30 nM, a qualitative analysis showed that more streptavidin adheres, based on relative fluorescence, to higher CPB concentration membrane surfaces, and that essentially no streptavidin binds to the membrane not containing CPB.

Di-ISE Protein Sensing Proof-of-Concept

Figure 5:
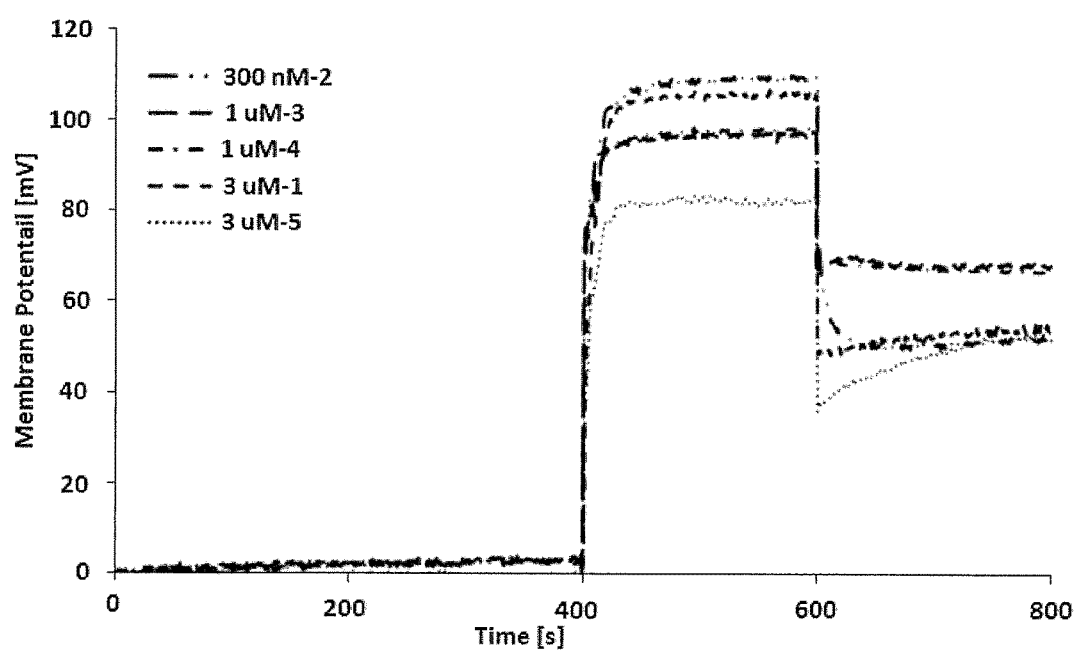
FIG. 5. Di-ISEs incubated for 30 min with streptavidin solution concentrations from 300 nM-3 µM. The Di-ISE contains 1 w % valinomycin +10 nM cholesterol-polyethylene glycol-biotin (CPB) conjugate on the K+ side of the membrane and 0.1 w % NaX di-ISE on the Na+ side of the membrane. On addition of streptavidin the voltage decreases as shown at ~600 sec.

The final experiments center on detection of ligand specific analyte binding and show that CPB on di-ISE membrane surfaces not only binds streptavidin, but also that binding results in further di-ISE voltage changes. FIG. 5 shows a CPB containing di-ISE in DI water to which K+ is added to a 0.1 M concentration with a corresponding voltage jump of 140 mV. The di-ISE was serially removed and incubated for 30 min intervals with successive aliquots of 300 μL of 300 nM Streptavidin-FITC solutions added to the 1% valinomycin + CPB side of membrane. The results show that when Streptavidin-FITC is added, the K+ side of the membrane is partially blocked as evidenced by a 20 mV drop in voltage due to partial coverage of the surface membrane available for receiving and then transporting K+ ions. Increasing durations of incubation with subsequent incubations all result in corresponding drops in voltages of 5-10 mV due to further coverage of the membrane surface with longer streptavidin-FITC solution incubation times. The net 40 mV drop in voltage corresponds to a theoretical membrane coverage of 93%. Given the 5.1 nm molecular size of streptavidin, there were total of $5.4 \times 10^{13}$ streptavidin molecules in 300 μL of 300 nM streptavidin solution, comparable to the initial $3.0 \times 10^{12}$ number of CPB molecules. The model showed that 84% of the CPB molecules have bound streptavidin. Thus, the experimental data confirmed the model. Importantly, this test shows that the di-ISE biosensors can be used to successfully detect proteins.

Conclusions

This example describes a new type of protein biosensor based on a modified ion selective electrode approach. A ligand-receptor concept is combined with a di-ISE to create a simple, fast responding and inexpensive protein biosensor. The di-ISE calibration curve results in a slope of 54.3 mV/log[K+], a limit of detection of $10^{-4}$ M, and the response time was less than 10 sec. The results show that with CPB as a ligand covering the di-ISE K+ ionophore side of the membrane, the di-ISE responds to streptavidin by drops in membrane potential. Moreover, the amount of protein bound to the surface and corresponding voltage shift can be correlated to a modification of the fundamental GHK equation used to describe transmembrane voltage responses in living neurons.

Example 2

Neuron-Like Dual Ionophore Ione-Selective Eletrode for Detecting Circulating Prostate Tumor Cells The cell-surface enzyme prostate—specific membrane antigen (PSMA) is the most important enzyme-biomarker and target in prostate cancer research. PSMA is a transmembrane protein up-regulated on the tumor cell surface of late-stage, androgen-independent, and metastatic prostate cancer. It has very unique enzymatic activity, and its crystal structure gives high resolution. These properties have enabled the development of various high-affinity chemical inhibitor scaffolds for this enzyme-biomarker. There is a need to employ the mechanism of inhibitor binding to PSMA and to build a simplified, fast and targeted sensor for PSMA detection.

This example describes a simple, quick and effective assay which is based on a dual ionophore Ion-selective Electrode (di-ISE is) coupled with an affinity assay mechanism. The exemplary di-ISE demonstrated here comprises a K+ ionophore and an Na+ ionophore in separated compartments of the same electrode constructed such that both compartments are exposed to the same solutions on either side of the membrane. The K+ ionophore side of the membrane contains a molecule that specifically binds PSMA, and the goal is to detect Prostate Circulating Tumor Cells (PCTCs). When opposing concentration gradients of K+ and Na+ are present, the system starts at a resting voltage that corresponds to the relative permeability of each ion species and concentration gradients. When cancer cells are present in solution and bind to the inhibitor on the membrane surface of one compartment in the di-ISE, e.g. the K+ ionophore side, the complex blocks at least a portion of that side of the dual compartment membrane, hindering the flow of K+ ions and changing the voltage. This example describes the methodology for creating such a sensor and provides data demonstrating its use.

Figure 6A:
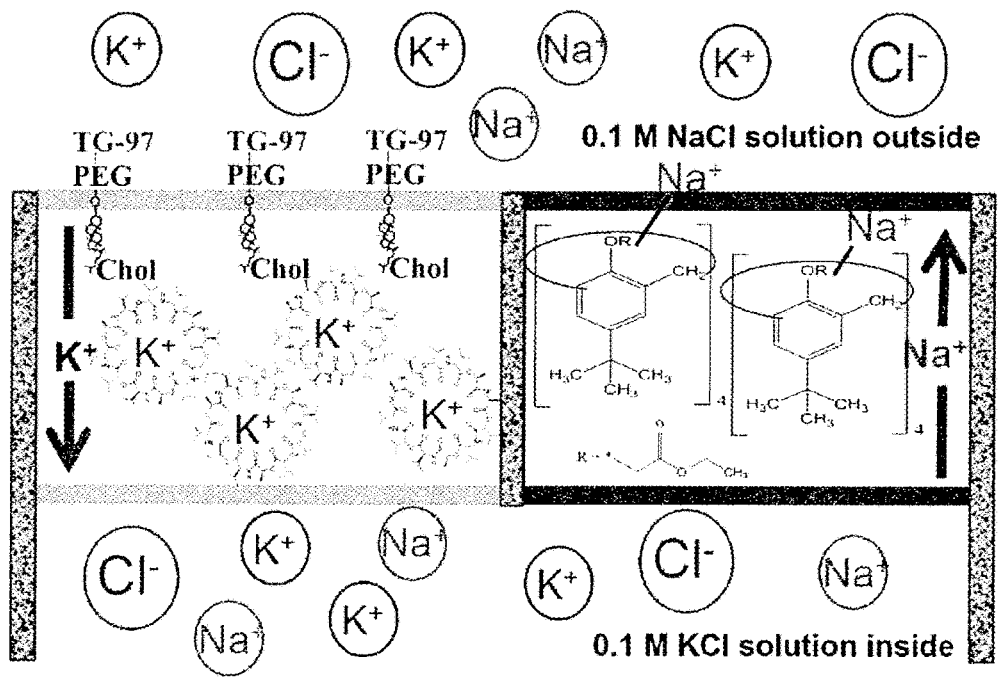
FIGS. 6A and B. Dual ionophore ion selective membrane for capturing Prostate Circulating Tumor Cells (PCTCs). (A) A dual ionophore ion-selective electrode (di-ISE) comprising two separate membrane chambers with common interior and exterior electrolytic fluids. The chamber on the left contains K+ ionophores inside the membrane and also contains the complex Cholesterol-PEG-TG97 (CPT) with cholesterol inserted in the membrane with a PEG-TG97 portion of the molecule facing away from the membrane. The right hand chamber contains Na+ ionophores. A resting potential is created by the opposing K+ and Na+ concentration gradients; (B) Capturing PCTC through prostate-specific membrane antigen (PSMA)-TG97 ligand-enzyme inhibitor receptor mechanics interferes with K+ ion transfer, resulting in a measurable membrane potential shift.
Figure 6B:
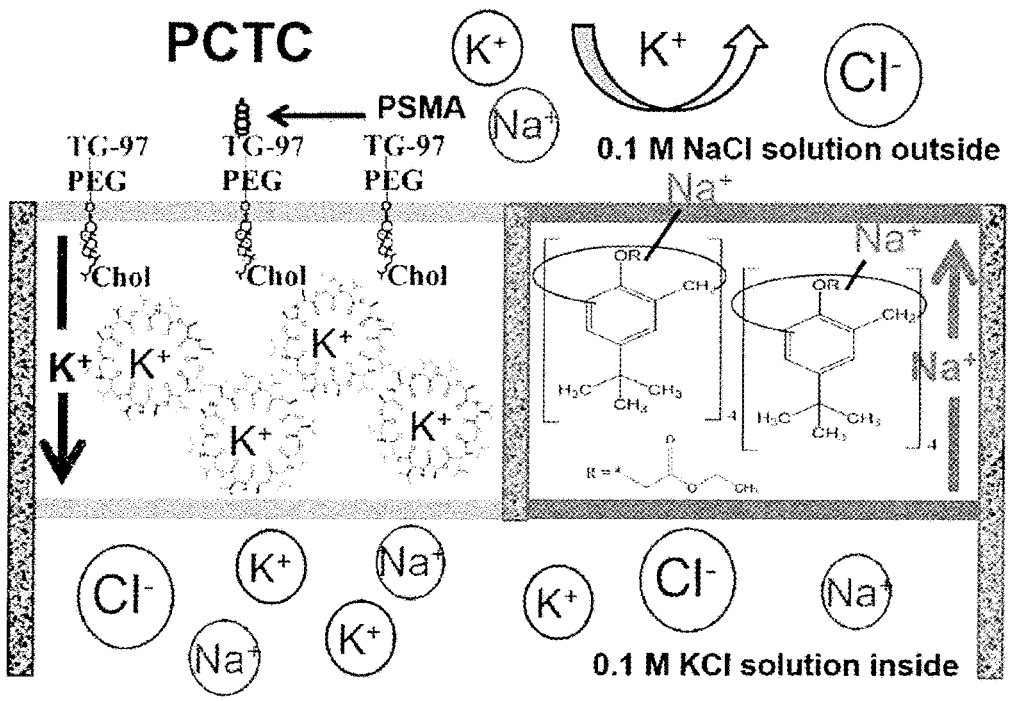

An exemplary Dual Ionophore ISE for detecting PCTCs is illustrated schematically in FIGS. 6A and B which are similar in construction to the design of FIG. 1. One compartment (on the left side as depicted) of the di-ISE is dedicated to K+ transport through the K+ selective ionophore valinomycin, and the other compartment (on the right as depicted) is dedicated to Na+ transport through the Na+ selective ionophore NaX. Exposing top and bottom sides of the two compartments to the same electrolyte solutions allows mimicry of the neuron in that transporting mechanisms are present for multiple ion types and relative permeabilities, which can be altered in the neuronal response, leading to large swings in transmembrane voltages on the order of 100 mV or more. Separating the two ionophores into two separate membrane compartments, in the present case, accomplishes the same purpose, only it allows one compartment to have a bioaffinity molecule such that when binding occurs, transport of only one ion type is altered, thereby modulating the transmembrane voltage in a way similar to a living neuron when one voltage gated ion channel is triggered over another. To apply the concept to PCTC detection, in some aspects, highly specific molecules such as the TG97 PSMA inhibitor, which binds to the PSMA active site, can be employed. To do this, an exemplary conjugate was synthesized by connecting the PSMA inhibitor to cholesterol through a polyethylene glycol (PEG) spacer arm, the new molecule being Cholesterol-PEG-TG97 or CPT. In the di-ISE, the K+ membrane side contained the CPT conjugates. As illustrated in FIG. 6A, when opposing concentration gradients of K+ and Na+ are present, the system starts at a resting voltage that corresponds to the relative permeability of each ion species and concentration gradient. As illustrated in FIG. 6B, when PCTCs are captured by CPT conjugates, K+ ion transport is inhibited, and the di-ISE detects the presence (and capture) of cancer cells based on the resulting changes in voltage.

Materials and Methods

Reagents

Reagents for making membranes were composed of high molecular weight Poly (vinyl chloride) (PVC) of Selectophore grade (Fluka), Dioctyl phthalate (DOP) (Aldrich), tetrahydrofuran (THF) (Fluka), benzene (Fisher Scientific Company), valinomycin, a K+ ionophore (A.G. Scientific, Inc.), and Sodium Ionophore X (NaX) (Fluka). The bioreceptor base molecule was cholesterol polyethylene glycol (PEG) NHS (molecular weight 1000, 5000, NANOCS). The TG97bioaffinity molecule, a PSMA enzyme inhibitor which was connected to the base molecule. Cell simulants were streptavidin coated silica microspheres with a 1.01 μm mean diameter (Bangs Laboratories, Inc.), and the florescent label was biotin FITC (Sigma Aldrich). Materials for constructing di-ISE cartridges included beverage clear Tygon® PVC tubing of 0.25" inner diameter and 0.375" outer diameter (Fisher brand), durable nylon tight-seal barbed tube fitting Wye connectors for 0.25" diameter tubing (McMaster-Carr), ethylene propylene diene monomer (EPDM) tapered plugs with a 0.188" small end and a 0.344" large end (Rubber Dynamics), 18G silver wire of 99.99% purity (Artbeads, Wash.), and $FeCl_3$/HCl PC-Board Etching solution to make Ag/AgCl electrodes (GC Thorson, Inc., Rockford, Ill.).

Synthesis of Cancer Cell Affinity Molecules

CPT conjugate was synthesized by combining cholesterol-PEG-NHS and $H_2$N-AH-TG97 using a standard coupling procedure [Ganguly, T., S. et al. Nuclear Medicine and Biology, 2015. 42(10): p. 780-787; Liu, T. C., et al. Prostate, 2008. 68(9): p. 955-964]. In brief, N-Hydroxysuccinimide (NHS) is an organic compound with the formula $C_4H_5NO$. The crosslinking reaction can be conducted in the presence of N-Hydroxysuccinimide. When there is an NHS-ester cross linker present, it will react with any compound containing a free amine.

Figure 7:
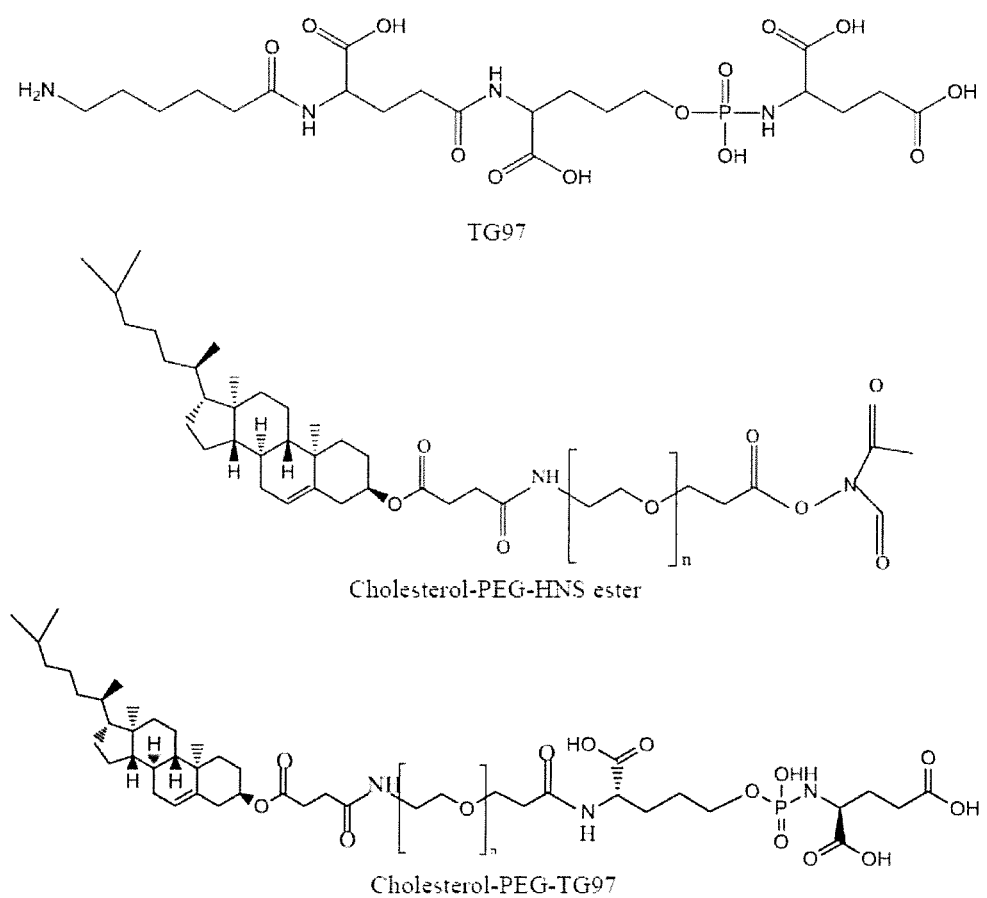
FIG. 7. Structures of PSMA inhibitor core TG97, Cholesterol-PEG-NHS and CPT conjugate, where n=1,000, but can be 4-5,000 or more depending on the application.

Cholesterol is an organic chemical substance classified as a waxy steroid of fat. Because of its properties and structure, cholesterol is very hydrophobic and soluble in the PVC-DOP membrane. Polyethylene glycol (PEG), a polyether compound makes PEG able to be used as a hydrophilic spacer. For synthesizing CPT conjugate, Cholesterol-PEG-NHS and $H_2$N-AH-TG97 were prepared. The Cholesterol-PEG-NHS ester is commercially available with various lengths. $H_2$N-AH-TG97 is a PSMA inhibitor core. Both structures are shown in FIG. 7. The two compounds react under conditions of room temperature, when placed in buffer of pH 8.3-8.5 for 8 hours. The ratio of TG97: Cholesterol-PEG-NHS ester is 2:1. The excess TG97 is reacted with an isothiocyanate resin to remove it from the mixture as a means of purification. The CPT conjugate is also depicted in FIG. 7.

Immobilization of CPT into PVC Membrane

Affinity Molecule Incorporation Protocol

The membrane solution was dissolved in THF with 66% DOP, 33% PVC and 1% ionophore. The PVC rod was drilled with a 0.32" diameter hole on one end had at the other end two 0.08" separated chambers. A 7 μL K+ ionophore membrane solution was applied to one chamber. After the K+ ionophore membrane was formed, the membrane was placed into 1 nM, 10 nM, and 100 nM CPT solutions for two days. Then 7 μL of Na+ ionophore membrane solution was applied to the other chamber. The electrode was ready when all membranes were dry.

Partitioning Protocol for Positioning Bioaffinity Molecules at di-ISE/Water Interface The extraction protocol to immobilize CPT and CPB into PVC membranes begins with a membrane cocktail made with 1.65 mg PVC, 3.3 mg DOP, 100 μL of benzene and 300 μL of THF. CPT or CPB powder was dissolved in water. A 500 μL aqueous solution of CPT or CPB at various concentrations was added to a 400 μL membrane cocktail in 1.5 mL Eppendorf tubes. The combined solution in Eppendorf tubes was vigorously shaken for 2 min and centrifuged at 12 rpm for 8 min. After 50 min in a sonicator, the tubes were opened in a closed ice bucket to slowly evaporate for about 1 week. Then the bottom of the Eppendorf tube was cut off and a thin membrane was formed on the top of the aqueous layer. After inverting the Eppendorf tube, the membrane was ready to use after washing with DI water.

Electrode Construction

The cell sensor di-ISEs were constructed with valinomycin ionophore at 1 wt % for the K+ side of the membrane and 0.1 wt % NaX for the Na+ side. The di-ISE consisted of a Y-shaped connector to connect two types of ionophore membranes, a silver wire of 0.04" diameter which was etched with ferric chloride to form an Ag/AgCl wire, and a tapered plug as a cap to seal the Ag/AgCl wire inside the electrode bodies. For CPB the di-ISEs were filled with 0.1 M NaCl, calibration solutions consisted of KCl administered through the standard addition method and streptavidin coated microspheres presented in 0.1 M KCl solution. For CPT di-ISEs, the filling solution was 0.1 M KCl and the soaking and calibration curve solutions were 0.1 M NaCl because the Na+ ion is consistent with the predominant ion in the cell buffer.

Apparatus

An inexpensive potentiometer for voltage measurements contained an eight-channel high input impedance 12 bit A/D converter (resolution was 0.62 mV), connected on a specially designed miniature (7 cm×4 cm×1 cm) board [Plesha, M. A., et al. Anal Chim Acta, 2006. 570(2): p. 186-194]. The potentiometer connected ISE electrodes and a reference electrode attached to pin receptacles and also converted electrical signals to digital signals for transference to a computer via a USB port. Excel was used to covert voltage data from digital readings, and data was normalized to a zero reading at $10^{-7}$ M K+ concentration.

Cell Lines, Cell Culture and Cell-Labeling

LNCaP (PSMA+) cells were grown in T-75 flasks with complete growth medium 1640 [RPMI 1640 containing 10% heat-inactivated fetal calf serum (FBS) and 1% penicillin] in a humidified incubator at 37° C. in a 5% $CO_2$ environment. After LNCaP cells were grown to approximately 70% confluence, they were washed twice with pre-warmed growth medium; then confluent cells were detached with 5 mL 0.25% HyClone™ Trypsin, 0.1% EDTA solution for 8 min at 37° C. The cell suspension was neutralized with 5 mL of complete growth medium. The LNCaP cells were then centrifuged at 900 x g at 4° C. for 5 min. Following removal of the medium, the cells were resuspended in 0.15 M NaCl, 50 mM HEPES, 1% FBS, pH 7.4 buffer at a concentration of 736,000 cells/mL as determined under a microscope with the aid of a hemocytometer.

Confocal Laser Scanning Microscopy

An LSM 510 META Laser Scanning Microscope was used with an argon laser to excite at 405 nm for 4',6-diamidino-2-phenylindole (DAPI), and an LP505 nm filter was used to collect the emission spectra.

Cell Biosensor Testing: Di-ISE Surface Coating Simulation Blocking Method Simulation The first method for simulating cell capture was simply blocking one side of the di-ISE by covering it with aluminum foil. The ionophore concentrations in the di-ISE were 1% valinomycin in the K+ ionophore compartment and 0.1% NaX in the Na+ ionophore compartment. The reference electrode and a di-ISE were connected to the NRL potentiometer system and calibrated in 50 mL DI $H_2O$ for 200 sec. Then 5600 µL of 1 M NaCl solution was added to make a final concentration of 0.1 M NaCl. After 200 sec, the Na+ ionophore compartment of the di-ISE membrane was taken out of solution, rinsed with DI $H_2O$, and covered by aluminum foil, then put back into solution. After another 200 sec, the K+ ionophore compartment was taken out of solution, rinsed with DI $H_2O$, and covered with aluminum foil; meanwhile the Na+ ionophore compartment covering was removed. After another 200 sec, both compartments of the membrane were removed and the di-ISE returned to the solution. After another 200 sec, the whole procedure was repeated one more time.

Di-ISE Capturing of Streptavidin Coated Microspheres

To prove that the di-ISE can capture cellular simulants, in this case streptavidin coated microspheres, the CPB molecule was inserted into the hydrophilic plasticizer contained in the di-ISE PVC polymer matrix and to serve as the bioaffinity agent. The PVC membrane surface was made by constituting CPB at 1 nM and 100 nM concentrations by dissolving it in dimethyl sulfoxide (DMSO) and DI $H_2O$ in 1:4 ratio.

To demonstrate capture of streptavidin coated microspheres, a concentration of $5.8\times10^7$ microspheres per 150 µL phosphate buffered saline (10× concentrated PBS) solution was incubated on the CPB compartment and non-CPB sides of di-ISE membranes at 37° C. for 30 min. After that, membranes were washed twice with pH 7.4 PBS buffer. Then 150 µL of 300 nM Biotin-FITC was added onto the membrane surfaces at 37° C. and incubated for 30 min. The membranes were then washed twice with pH 7.4 PBS buffer. The fluorescently labeled membranes were scanned by confocal laser scanning microscopy under a 25× objective to confirm membrane-microsphere binding.

Once done microsphere capture was demonstrated, experiments on di-ISEs with CPB on the K+ side of the membrane were made to prove that when di-ISE membrane binds streptavidin coated microspheres, the electrode signal is affected. The standard di-ISE construction protocol was used with 1% valinomycin on the K+ compartment side of the membrane and 0.1% NaX on the other side. The di-ISE was calibrated in 50 mL DI $H_2O$ until the voltage reached an equilibrium value. Then 1 M KCl solution was added in DI $H_2O$ to reach a final concentration of 0.1 M KCl. Next the di-ISE was pulled out of solution, and 150 µL of solution containing $5.8\times10^7$ microspheres per 150 µL was added onto the 1% valinomycin membrane side and incubated for 30 min. The di-ISE was put back into the test solution and the new equilibrium voltage recorded. Then another 150 µL solution containing $5.8\times10^7$ microspheres per 150 µL was added onto the K+ ionophore side of the membrane and incubated for 30 min and reinserted into solution to assess further changes in di-ISE voltage.

Di-ISE Characterization and Behavior Modeling

The electrode calibration curve was measured using the NRL potentiometer device at room temperature. For the cell biosensor, both 1 wt % valinomycin//0.1 wt % NaX di-ISEs and 1 wt % valinomycin+1000 nM CPT//0.1 wt % NaX di-ISEs were tested where the symbol "//" separates the two sections of electrically connected membranes. Both membrane sides of the electrode were dipped into a continuously stirred crucible containing 50 mL of deionized nano-pure (DI) water. For all tests, the reference electrode was filled with 3 M NaCl. The standard addition method (SAM) was used for linearity and limit of detection (LOD) studies for Na+ concentrations from $10^{-7}$ M up to $10^{-1}$ M.

The model and equations used were described in Example 1 (Equations (1) and (2)). Di-ISE Capturing of LNCaP Cells Two methods for incorporation of CPT were used to make di-ISEs to test for capture of cells, adsorption and extraction. The adsorption di-ISEs were made with 1.0 w % valinomycin in one di-ISE compartment and 0.1 w % NaX in a second compartment, soaked in 6.5 μM concentrations of CPT. After membranes were made, di-ISEs were soaked in cell buffers before experiments. The extraction membranes were made with 1 nM, 10 nM, 100 nM and 1000 nM CPT concentrations with membrane cocktail. A total of 200 μL of $6.8 \times 10^5$ LNCaP cells was added onto the membrane surface and incubated at 37° C. for 30 min. Then membranes were washed with HEPES buffer three times. Then 200 μL of 7.25 μL DAPI mixed with formaldehyde was added on each membrane for 5 min. The extraction di-ISEs, also consisting of 1.0 w % valinomycin and 0.1 w % NaX, were made with 1 nM, 10 nM, 100 nM and 1000 nM concentrations of CPT within the membrane cocktail on the K+ ionophore compartment side of the membrane. The di-ISEs were filled with 0.1 M KCl and soaked in 0.1 M NaCl. The di-ISEs were calibrated in 50 mL DI $H_2O$ for 10 min before adding either KCl or NaCl solutions to 0.1 M concentrations. For the extraction di-ISEs, after the di-ISEs were calibrated, the solution was switched to HEPES buffer. After the di-ISEs were calibrated in HEPES, there were two ways of adding cells to the electrodes. One was by pre-incubation of 200 μL $5.9 \times 10^5$ cells on the K+ ionophore compartment side of the membrane at 37° C. for 30 min. Electrode voltages were measured and recorded as a function of time. After successful signal changes were shown, the fluorescent dye DAPI in formaldehyde was added onto the membrane surface and fluorescent labeled membranes were scanned by confocal laser scanning microscopy to confirm cell-surface binding.

Results and Discussion

Di-ISE Surface Coating Simulation: Cell Blocking Surface Simulation

This experiment simulated di-ISE usage in biological environments for detecting cells and to demonstrate sensing as well as to identify an ideal operating mode for cellular biosensing. With an inside solution consisting of 0.1 M KCl, the di-ISE was equilibrated in 50 mL $H_2O$. When NaCl solution was added to bring the outside solution to 0.1 M NaCl concentration, the equilibrium was shifted (not shown) as NaX ionophores carry Na+ into the di-ISE through the Na+ compartment of the membrane system. Because the valinomycin concentration in the counterpart compartment is 10× higher than the NaX concentration, the permeability for transport of Na+ ions outside to inside is ~10× lower than that for transporting K+ ions from inside to outside. However, valinomycin also can carry secondary Na+ ions and likewise NaX K+ ions with a much lower selectivity than for the primary ions. Equilibrium potentials jumped to ~35 mV. When covering the Na+ side of the membrane, NaX is no longer available for transport of Na+ ions, causing the di-ISE potential to decrease on average to 14 mV. Remarkably, when the Na+ compartment was unblocked and the K+ membrane compartment covered, there was a huge potential increase to a value of 215 mV. Because valinomycin could no longer transport K+ ion from the opposite (inside) direction and the voltage previously was shifted far toward the resting K+ potential by nature of the fact that valinomycin concentration is ~10× over that of NaX, a large swing to the Na+ potential occurs. This simulates what happens when a neuron is stimulated, K+ channels are at first blocked while ion channels open for Na+ to flow from outside to inside the cell to create the rising phase of an action potential. Then, when the Na+ side and K+ side were both uncovered, the potential, dropped to 54 mV. This has particular meaning for cellular biosensing as the predominant ion in cell suspensions is typically Na+. Having a di-ISE with a 10× higher valinomycin ionophore concentration causes the sensor to begin at a K+ resting potential, outside positive. Adding a Na+ solution causes only a slight inward flux of Na+ compared to the K+ outward flux by nature of the relative concentrations of each ionophore. However, on cell binding, as simulated by coverage of the K+ membrane compartment, the large initial K+ outward flux is significantly diminished, thereby shifting the potential largely in the positive direction. However, after the two membrane compartments have had some time to be exposed to both ion types, the Na+ and K+ occupation ratios for the valinomycin and NaX ionophores are in proportion to their relative selectivities.

The next experimental aim was to determine whether di-ISE membranes could capture streptavidin coated microspheres with the intent of having them serve as simulants for cell binding. Microscopy images (not shown) revealed that the fluorescent microspheres aggregate on binding with no obvious difference between membranes without and with CPB concentrations from 1 to 100 nM; thus, all membranes may be used to capture microspheres. The relative quantities of specific binding and non-specific binding is difficult to analyze. However, this experiment shows the membrane surface has the ability to bind microspheres from solutions containing them and that despite variations in CPB concentrations, at least in the ranges tested all membranes appear to show 40-50% coverage with beads. While we expected to be able to differentially capture varying amounts of beads, the fact that beads bind evenly to CPB membranes without CPB offers the advantage modeling di-ISE capture microspheres and evaluating changes in membrane potential as a result, especially if we only expose one side of the two-compartment di-ISE to the microsphere solutions.

Figure 8:
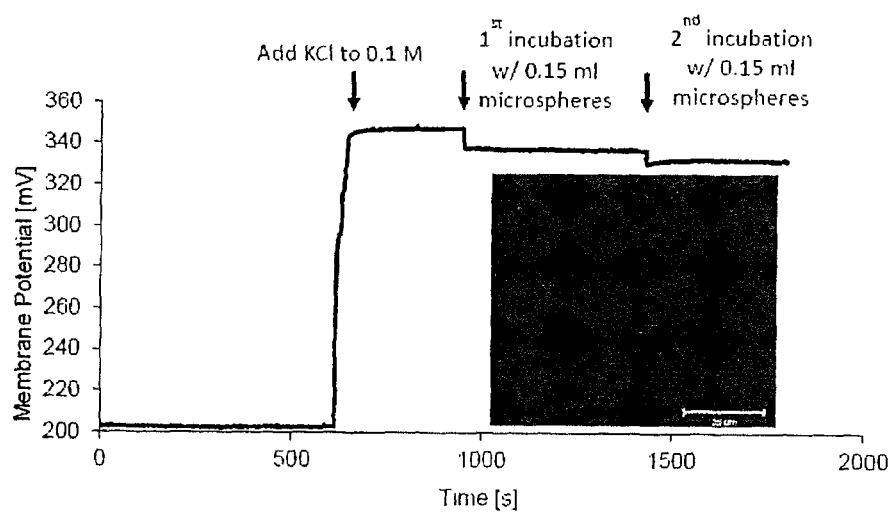
FIG. 8. Streptavidin coated microsphere beads attached on the di-ISEs membrane surface. The di-ISE consisted of two compartments, one with 1 w % valinomycin and the other with 0.1 w % NaX. KCl was added to a final concentration at 0.1 M. After equilibration, 1st and 2nd microsphere incubations on the valinomycin compartment show successive 10 and 7 mV drops in membrane potentials coinciding with increased microsphere capture. The inset shows a photomicrograph of the membrane.

Immediately after the di-ISE results were obtained, the coated membrane was taken for scanning under the microscope. The image was taken under transmitted light without any fluorescence, showing that microspheres were bound by the membrane. Given a membrane average surface area of 51.5 $mm^2$ and a diameter of the microsphere of 1.01 the calculated number of microspheres to cover the whole surface if there is no overlap is $6.4 \times 10^7$, theoretically. Given that the 150 μL solution theoretically contained $5.8 \times 10^7$ microspheres there are sufficient microspheres available for this to happen. However, the photo showed microspheres were not evenly distributed on the membrane surface, but were clustered instead. This should be the reason that K+ ionophore side of membrane was only partially blocked. Only some K+ ions were prevented from crossing the membrane. The signal was affected, but not as much as when the membrane is totally blocked as shown in prior results (e.g. Example 1). The results are depicted in FIG. 8.

Characterization

The basic properties of the new protein di-ISEs containing CPT, were evaluated experimentally and by nonlinear curve fitting of calibration curves to an Equation (1) di-ISE model. The calibrations curves for di-ISE responses to K+ concentration step increases in the outside solution, with and without CPT on the surface showed that the CPT electrode responds to step changes in K+ concentration with the speed and sensitivity characteristic of typical ISEs with response times, defined as the time to reach 95% of the steady state EMF, of 21 sec and 32 sec respectively, for the non-CPT and the CPT containing di-ISEs. The slopes of di-ISE calibration curves without and with CPB are in agreement with values of 16.4, and 16.3, respectively. From the calculated size of CPT, based on a width of PEG of $8.66 \times 10^{-8}$ mm, and length of PGE-TG97 of $3.77 \times 10^{-5}$ mm, the number of CPTs that would cover the membrane surface would be $1.6 \times 10^{13}$ molecules. For this di-ISE with 1 µM CPT on the K+ side of the membrane, the number of CPT molecules available are $3 \times 10^{14}$. From these calculations, if all CPTs were facing out of the membrane, the membrane surface would be saturated. However, based on a model fit of the CPT calibration curve with a membrane potential 5.6 mV below the non-CPT curve at 0.1 M Na+, the model in Eq (1) fits the data when a value is 0.8 or as if 80% of the surface is covered for the case with 1 µM CPT on K+ side of the membrane. Presumably the CPT molecules have their polyethylene strands facing outward into the solution in which case a calculation based on just the size of the cholesterol molecule, having a molecular length of $3.8 \times 10^{-5}$ mm, width of $8.7 \times 10^{-8}$ mm, shows that with a 51.5 mm$^2$ membrane area that $1.6 \times 10^{13}$ molecules can theoretically imbed themselves at the membrane interface. Of course some CPT molecules may be contained within the membrane itself or may have migrated to the inside of the membrane. Nevertheless, the important point is that as a significant number of K+ molecules are still able to diffuse through the CPT, transport occurs across the surface to some extent and influences the transmembrane potential.

Di-ISE Capturing of LNCaP Cells

The di-ISE data from experiments performed with the K+ membrane compartment adsorption protocol offer insights on the effectiveness of this procedure. Calibration curves for di-ISEs made by membrane-capture of CPT molecules by exposure of the membranes to solutions containing 6.5 µM concentrations of CPT were similar to that of the blank or control di-ISE as the CPT data deviated from the control by less than 2.6% at a 0.1 M K+ concentration, and overall non-capture results agree to within a relative standard deviation of 7.6% on average around the mean value for the collective data set. The reason for this is that the CPT adsorption does not result in a surface concentration high enough to affect the membrane surface availability to the solution containing K+ ionophores. To achieve higher concentrations it is necessary to mix CPT directly into the membrane cocktail and enhance its migration to one side of a membrane by exposing one side to an aqueous phase while the membrane is forming as was done in the previous sections.

Figure 9:
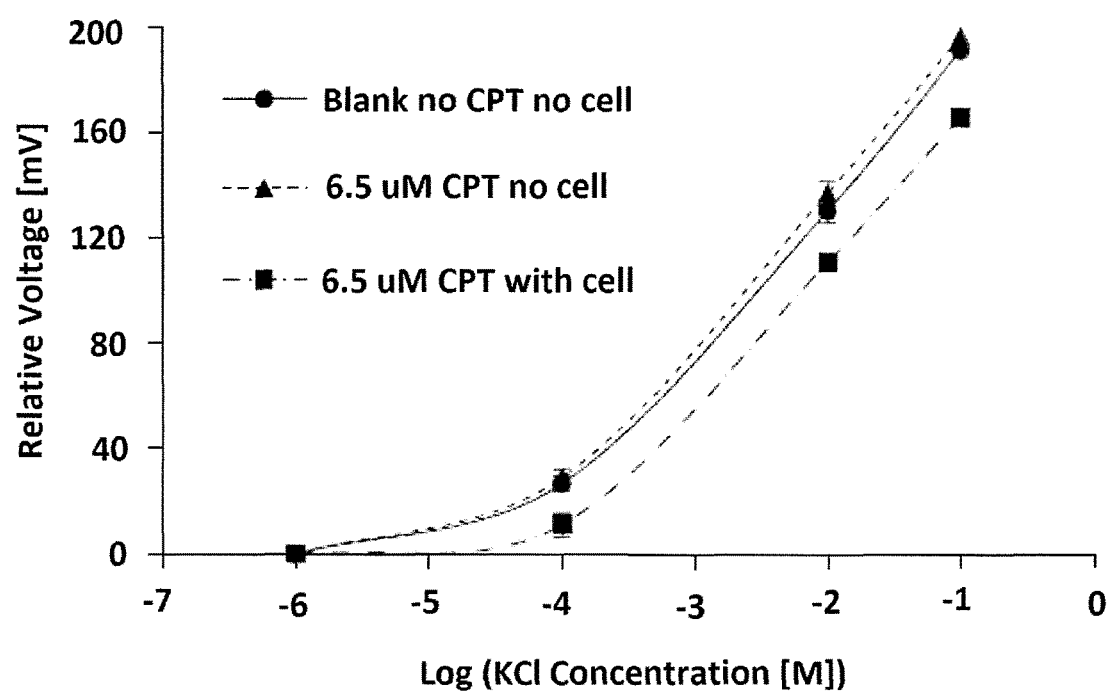
FIG. 9. Demonstration of di-ISE capture and sensing of LNCaP cells. Blank di-ISEs without CPT are compared to di-ISEs exposed to 6.5 µM CPT. The CPT membranes show a reduction in voltage on exposure to LNCaPs while the control (blank) showed no change in calibration results when compared to the curve for the blank di-ISE for exposure to increasing concentrations of K+. Blank (N=10), 6.5 µM CPT (N=13), 6.5 µM CPT with LNCaP cells (N=6).

More importantly, CPT, when it does imbed in the membrane surface, is able to capture cells. The results, shown in FIG. 9, showed that there is a drop in potential of 30 mV in the 0.1 M K+ solution. This drop is associated with a theoretical surface coverage of 10% when determining the effective surface area multiplier a through a nonlinear curve fit of Eq. 1.

The next step in testing di-ISE ability to capture cells with CPT was to assess results when CPT is mixed directly in the membrane cocktail. When 200 µL of 68,000 LNCaP cells were incubated on different membranes containing concentrations of CPT of 0, 1, 10, 100, 1000 nM, based on relative fluorescence, higher CPT concentration membranes showed increased cell adsorption. No CPT membrane shows complete coverage and blank di-ISEs show some non-specific binding.

Figure 10:
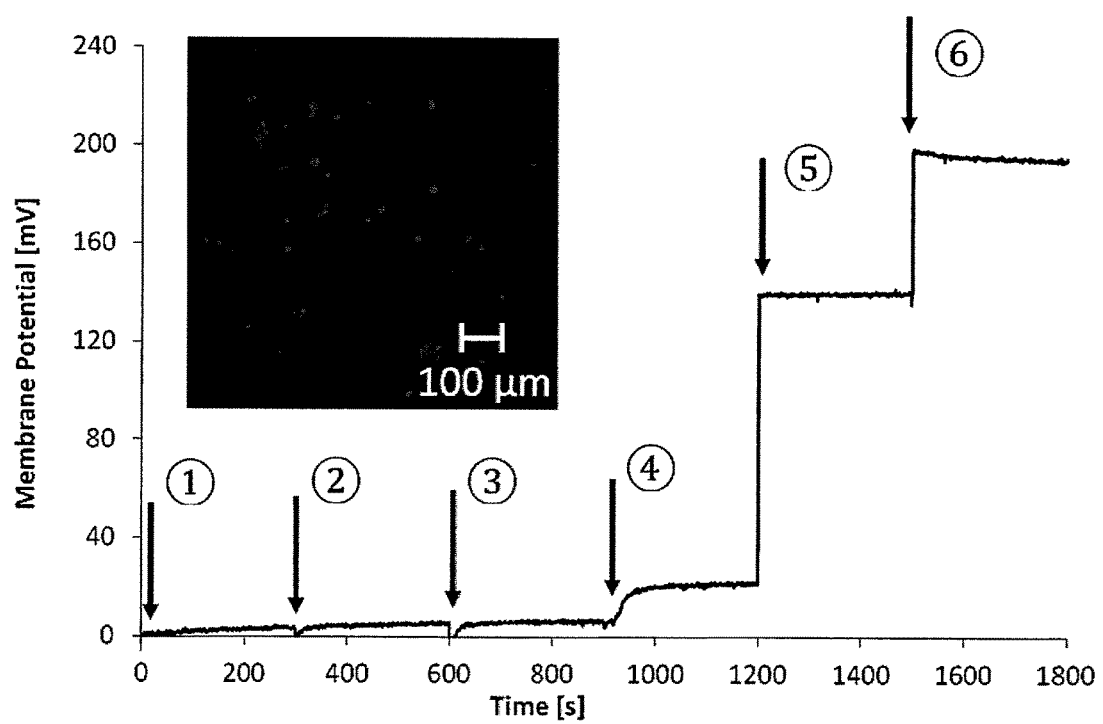
FIG. 10. Calibration curve with LNCaP incubation on di-ISE-CPT containing membrane shows step voltage increases. The di-ISE contains 1 wt % valinomycin +1 µM CPT on the K+ side of membrane and 0.1 wt % NaX di-ISE on the other side. Filling solution is 0.1 M KCl. ① 50 mL DI H2O calibration followed by standard additions of NaCl to ② 0.001 M; ③ 0.01 M; and ④ 0.1 M NaCl; ⑤ shows the change calibration solution to HEPES buffer; and ⑥ the response after incubating the K+ side of the di-ISE for 30 min with 200 µL of HEPES buffer solution containing 5.9×105 LNCaP cells.

In addition, for testing of the electrodes the membrane solutions were reversed such that the outside solution was a physiological buffer (sodium salt, pH 7.4) like that which contains viable cells. FIG. 10 shows that when CPT containing di-ISE in DI water to which Na+ is added in increments to 0.001, 0.01 and 0.1 M concentrations, respectively, a corresponding final voltage of 20 mV above baseline was achieved as the NaX side of the di-ISE carried Na+ across the membrane to counter the opposing K+ gradient, which is consistent with the results observed for CPT di-ISEs. Using HEPES buffered medium is common in live cell experiments and results obtained when the di-ISE solution was replaced with HEPES buffer containing 1 M Na+ solution and calibrated for 300 sec showed a large voltage jump of 120 mV as the di-ISE reached a new equilibrium. Then the di-ISE was removed and incubated for 30 min with 200 µL of 1M HEPES containing $5.9 \times 10^5$ LNCaP cells. After cell incubation on the K+ side of di-ISE, the membrane was partially blocked as evidenced by a 57 mV increase in voltage. This result agrees with results from the cell blocking surface simulation described earlier. Because the K+ side of the di-ISE membrane has an abundance of valinomycin, when it is partially blocked, the ability of valinomycin to transport K+ ion from the inside outward is substantially decreased. Therefore, the NaX can transport Na+ from outside the membrane to the inside, and the voltage is increased moving toward the Na+ equilibrium potential.

Blockade of the valinomycin side of the di-ISE coincides with theory and was supported by microscopy evidence. First, the 57 mV rise after incubating with LNCaPs corresponds to an equation (2) a value 0.01 or 99% coverage of the valinomycin membrane compartment. After testing di-ISE capture of LNCaP cells, 200 µL of 7.25 µM TG97-FITC was added onto the membranes, and after incubation and washing membranes containing CPT indeed showed adsorption of the fluorescently labeled LNCaPs when viewed under a microscope. However, the entire surface was not fluorescent. The diameter of LNCaP cells is around 25 µm and according to calculations, the total number of $1.05 \times 10^5$ LNCaPs incubated is more than the number needed to completely cover the membrane surface if all cells were captured. Given that the average length of PEG-TG97 is $3.77 \times 10^{-5}$ mm, and the average width is $8.66 \times 10^{-8}$ mm, $1.58 \times 10^{13}$ CPT molecules would cover the membrane surface even if the PEG-TG97 is oriented so it is laying down on the surface rather than protruding into the solution (more likely). Hence, given a CPT concentration of 1 µM in making of the di-ISE, $3.01 \times 10^{14}$ CPT molecules are theoretically available, more than enough to capture all the LNCaPs. However, the reason fewer cells were captured could be because after incubation some cells were gathered around the edge of the membrane, and/or many are desorbed and washed off during stirring (e.g. when the di-ISE is returned to the beaker containing HEPEs buffer).

Conclusion

Based on the results presented, first on coverage of one side of the di-ISE, then on microsphere and cell capture, a new fast, sensing system has been created that was inspired by living system neurophysiology in which transmembrane voltages are correlated to capture of cells or cellular simulants. One compartment of the di-ISE is made specific for cells or cell simulants via affinity ligand complexes imbedded in a hydrophobic membrane surface; this side of the di-ISE is specific for one ion type, in this case K+. A second ionophore contained in a separate compartment of the same di-ISE provides sufficient base current; even though primary K+ ions are blocked from entry into the first side of the di-ISE (e.g. by binding of a molecule of interest), to allow transmembrane voltages to be measured. From characterization results, the response times for di-ISEs without and with the capture molecule CPT are 28 sec and 42 sec, respectively. These results show that di-ISE cell biosensors can be used to successfully sense and measure the concentration of proteins.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:

1. A dual ionophore ion selective electrode (di-ISE) for detecting non-ionic molecules, macromolecules and cells, comprising
   I. a first chamber comprising a first membrane that is permeable to a first ion, wherein the first chamber contains an organic fluid comprising first ion ionophores, and
   II. a second chamber comprising a second membrane that is permeable to a second ion wherein the second chamber contains an organic fluid comprising second ion ionophores;
   wherein:
   the first membrane and the second membrane share a common exterior electrolytic fluid solution comprising the first ion;
   the first membrane and the second membrane share a common interior electrolytic fluid solution comprising the second ion; and
   the first membrane has an immobilized ligand specific for a binding site on the non-ionic molecule, macromolecule or cell, the immobilized ligand being located on a side facing the exterior electrolytic fluid solution.

2. The di-ISE of claim 1, wherein the immobilized ligand is specific for Prostate Circulating Tumor Cells (PCTCs).

3. The di-ISE of claim 1, wherein the first ion is K+ and the second ion is Na+.

4. The di-ISE of claim 3, wherein the first ion ionophores are valinomycin and the second ion ionophores are sodium ionophore X (NaX).

5. The di-ISE of claim 1, wherein the binding site is prostate-specific membrane antigen (PSMA).

6. The di-ISE of claim 1, wherein the immobilized ligand is TG97.

7. The di-ISE of claim 6, wherein the TG97 is in the form of Cholesterol-PEG-TG97 (CPT).

8. A method of detecting PCTCs in a biological sample from a subject in need thereof, comprising
   A. providing a dual ionophore ion selective electrode (di-ISE) for detecting prostate cancer cells, comprising
      I. a first chamber comprising a first membrane that is permeable to a first ion, wherein the first chamber contains an organic fluid comprising first ion ionophores, and
      II. a second chamber comprising a second membrane that is permeable to a second ion, wherein the second chamber contains an organic fluid comprising second ion ionophores;
      and wherein:
      the first membrane and the second membrane share a common exterior electrolytic fluid solution comprising the first ion;
      the first membrane and the second membrane share a common interior electrolytic fluid solution comprising the second ion; and
      the first exterior membrane has an immobilized ligand for a binding site on PCTCs, the immobilized ligand being located on a side facing the exterior electrolytic fluid solution;
   B. measuring a baseline voltage generated by the di-ISE;
   C. contacting the first membrane with the biological sample on the exterior side for a period of time and under conditions which allow PCTCs present in the biological sample to bind to the immobilized ligand; and
   D. detecting a change in voltage upon said step of contacting, wherein a change in voltage is indicative of the binding of PCTCs to the exterior side of the first membrane and the presence of PCTCs in the biological sample.

9. The method of claim 8, wherein the first ion is K+ and the second ion is Na+.

10. The method of claim 9, wherein the first ionophores are valinomycin and the second ionophores are sodium ionophore X (NaX).

11. The method of claim 8, wherein the binding site is prostate-specific membrane antigen (PSMA).

12. The method of claim 8, wherein the immobilized ligand is TG97.

13. The method of claim 12, wherein the TG97 is in the form of Cholesterol-PEG-TG97 (CPT).

* * * * *